(12) United States Patent
Daigle et al.

(10) Patent No.: US 7,521,217 B2
(45) Date of Patent: Apr. 21, 2009

(54) CARBONIC ANHYDRASE HAVING INCREASED STABILITY UNDER HIGH TEMPERATURE CONDITIONS

(75) Inventors: Richard Daigle, Charny (CA); Marc Desrochers, Quebec (CA)

(73) Assignee: CO2 Solution, Inc., Quebec (CA)

( * ) Notice: Subject to any disclaimer, the term of this patent is extended or adjusted under 35 U.S.C. 154(b) by 0 days.

(21) Appl. No.: 11/409,487

(22) Filed: Apr. 20, 2006

(65) Prior Publication Data

US 2006/0257990 A1 Nov. 16, 2006

Related U.S. Application Data

(60) Provisional application No. 60/673,345, filed on Apr. 21, 2005.

(51) Int. Cl.
*C12N 9/88* (2006.01)
*C12N 15/00* (2006.01)
*C12P 21/06* (2006.01)
*C07H 21/04* (2006.01)

(52) U.S. Cl. .................. 435/232; 435/69.1; 435/320.1; 536/23.2

(58) Field of Classification Search ........................ None
See application file for complete search history.

(56) References Cited

FOREIGN PATENT DOCUMENTS

| CA | 2 291 785 | 12/1998 |
|----|-----------|---------|
| CA | 2 329 113 | 6/2002 |
| CA | 2 393 016 | 1/2003 |

OTHER PUBLICATIONS

Ferrell et al., Amino acid sequence of rabbit carbonic anhydrase II. Biochim. Biophys. Acta., 1978, vol. 533: 1-11. (only SEQ ALGN).*
Strausberg et al., Generation and initial analysis of more than 15,000 full-length human and mouse cDNA sequences. PNAS., 2002, vol. 99: 16899-16903. (only SEQ ALGN).*
Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Guo et al., Protein tolerance to random amino acid change. Proc.Nat. Acad. Sci., 2004, vol. 101 (25): 9205-9210.*
Ferrell et al., Amino acid sqeuence of rabbit carbonic anhydrase II. Biochim. Biophys. Acta, 1978, vol. 533: 1-11.*
Whisstock et al., Prediction of protein function from protein sequence. Q. Rev. Biophysics., 2003, vol. 36 (3): 307-340.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Hunt, Jennifer A. et al., "Selection of Carbonic Anhydrase Variants Displayed on Phage", The Journal of Biological Chemistry, 1997, pp. 20364-20372, vol. 272, No. 33, The American Society for Biochemistry and Molecular Biology, Bethesda, MD, U.S.A.
Jackman, Jane E. et al., "Disruption of the Active Site Solvent Network in Carbonic Anhydrase II Decreases the Efficiency of Proton Transfer", Biochemistry, 1996, pp. 16421-16428, vol. 35, ACS Publications, U.S.A.
Scolnick, Laura R. et al., "X-Ray Crystallographic Studies of Alanine-65 Variants of Carbonic Anhydrase II Reveal the Structural Basis of Compromised Proton Transfer in Catalysis", Biochemistry, 1996, pp. 16429-16434, vol. 35, ASC Publications, U.S.A.
Krebs, Joseph F. et al., "Kinetic and Spectroscopic Studies of Hydrophilic Amino Acid Substitutions in the Hydrophobic Pocket of Human Carbonic Anhydrase II", Biochemistry, 1993, pp. 4496-4505, vol. 32, ASC Publications, U.S.A.
Saul B. Needleman et al., A General Method Applicable to the Search for Similarities in the Amino Acid Sequence of Two Proteins, J. Mol. Biol., vol. 48, p. 443-453, (1970).
Steven Henikoff et al., Amino Acid Substitution Matrices From Protein Blocks, Proc. Natl. Acad. Sci. USA, vol. 89, p. 10915-10919 (Nov. 1992).

* cited by examiner

*Primary Examiner*—Richard Hutson
*Assistant Examiner*—Ganapathirama Raghu
(74) *Attorney, Agent, or Firm*—Ware, Fressola, Van Der Sluys & Adolphson, LLP

(57) ABSTRACT

The present invention relates to polynucleotide and polypeptide sequences of carbonic anhydrase variants having increased stability under high temperature conditions compared to native carbonic anhydrase.

3 Claims, 21 Drawing Sheets

FIGURE 6

| Met 1 | Ser 2 | His 3 | His 4 | Trp 5 | Gly 6 | Tyr 7 | Gly 8 | Lys 9 | His 10 |
|---|---|---|---|---|---|---|---|---|---|
| Asn 11 | Gly 12 | Pro 13 | Glu 14 | His 15 | Trp 16 | His 17 | Lys 18 | Asp 19 | Phe 20 |
| Ile 21 | Ile 22 | Ala 23 | Lys 24 | Gly 25 | Glu 26 | Arg 27 | Gln 28 | Ser 29 | Pro 30 |
| Val 31 | Asp 32 | Ile 33 | Asp 34 | Thr 35 | His 36 | Thr 37 | Ala 38 | Lys 39 | Tyr 40 |
| Asp 41 | Pro 42 | Ser 43 | Leu 44 | Lys 45 | Pro 46 | Leu 47 | Ser 48 | Val 49 | Ser 50 |
| Tyr 51 | Asp 52 | Gln 53 | Ala 54 | Thr 55 | Ser 56 | Leu 57 | Arg 58 | Ile 59 | Leu 60 |
| Asn 61 | Asn 62 | Gly 63 | His 64 | Ala 65 | Phe 66 | Asn 67 | Val 68 | Glu 69 | Phe 70 |
| Asp 71 | Asp 72 | Ser 73 | Gln 74 | Asp 75 | Lys 76 | Ala 77 | Val 78 | Leu 79 | Lys 80 |
| Gly 81 | Gly 82 | Pro 83 | Leu 84 | Asp 85 | Gly 86 | Thr 87 | Tyr 88 | Arg 89 | Leu 90 |
| Ile 91 | Gln 92 | Phe 93 | His 94 | Phe 95 | His 96 | Trp 97 | Gly 98 | Ser 99 | Leu 100 |
| Asp 101 | Gly 102 | Gln 103 | Gly 104 | Ser 105 | Gly 106 | His 107 | Thr 108 | Val 109 | Asp 110 |
| Lys 111 | Lys 112 | Lys 113 | Tyr 114 | Ala 115 | Ala 116 | Glu 117 | Leu 118 | His 119 | Leu 120 |
| Val 121 | His 122 | Trp 123 | Asn 124 | Thr 125 | Lys 126 | Tyr 127 | Gly 128 | Asp 129 | Phe 130 |
| Gly 131 | Lys 132 | Ala 133 | Val 134 | Gln 135 | Gln 136 | Pro 137 | Asp 138 | Gly 139 | Leu 140 |
| Ala 141 | Val 142 | Leu 143 | Gly 144 | Ile 145 | Phe 146 | Leu 147 | Lys 148 | Val 149 | Gly 150 |
| Ser 151 | Ala 152 | Lys 153 | Pro 154 | Gly 155 | Leu 156 | Gln 157 | Lys 158 | Val 159 | Val 160 |
| Asp 161 | Val 162 | Leu 163 | Asp 164 | Ser 165 | Ile 166 | Lys 167 | Thr 168 | Lys 169 | Gly 170 |
| Lys 171 | Ser 172 | Ala 173 | Asp 174 | Phe 175 | Thr 176 | Asn 177 | Phe 178 | Asp 179 | Pro 180 |
| Arg 181 | Gly 182 | Leu 183 | Leu 184 | Pro 185 | Glu 186 | Ser 187 | Leu 188 | Asp 189 | Tyr 190 |
| Trp 191 | Thr 192 | Tyr 193 | Pro 194 | Gly 195 | Ser 196 | Leu 197 | Thr 198 | Thr 199 | Pro 200 |
| Pro 201 | Leu 202 | Leu 203 | Glu 204 | Cys 205 | Val 206 | Thr 207 | Trp 208 | Ile 209 | Val 210 |
| Leu 211 | Lys 212 | Glu 213 | Pro 214 | Ile 215 | Ser 216 | Val 217 | Ser 218 | Ser 219 | Glu 220 |
| Gln 221 | Val 222 | Leu 223 | Lys 224 | Phe 225 | Arg 226 | Lys 227 | Leu 228 | Asn 229 | Phe 230 |
| Asn 231 | Gly 232 | Glu 233 | Gly 234 | Glu 235 | Pro 236 | Glu 237 | Glu 238 | Leu 239 | Met 240 |
| Val 241 | Asp 242 | Asn 243 | Trp 244 | Arg 245 | Pro 246 | Ala 247 | Gln 248 | Pro 249 | Leu 250 |
| Lys 251 | Asn 252 | Arg 253 | Gln 254 | Ile 255 | Lys 256 | Ala 257 | Ser 258 | Phe 259 | Lys 260 |

FIGURE 7 (SEQ ID NO 2)

```
Met Ser His His Trp Gly Tyr Gly Lys His Asn Gly Pro Glu His
             5              10                 15
Trp His Lys Asp Phe Pro Ile Ala Lys Gly Glu Arg Gln Ser Pro
             20              25                 30
Val Asp Ile Asp Thr His Thr Ala Lys Tyr Asp Pro Ser Leu Lys
             35              40                 45
Pro Leu Ser Val Ser Tyr Asp Gln Ala Thr Ser Leu Arg Ile Leu
             50              55                 60
Asn Asn Gly His Thr Phe Asn Val Glu Phe Asp Asp Ser Gln Asp
             65              70                 75
Lys Ala Val Leu Lys Gly Pro Leu Asp Gly Thr Tyr Arg Leu
             80              85                 90
Ile Gln Phe His Phe His Trp Gly Ser Leu Asp Gly Gln Gly Ser
             95              100                105
Glu His Thr Val Asp Lys Lys Tyr Ala Ala Glu Leu His Leu
             110             115                120
Val His Trp Asn Thr Lys Tyr Gly Asp Phe Gly Lys Ala Val Gln
             125             130                135
Gln Pro Asp Gly Leu Ala Val Leu Gly Ile Phe Leu Lys Val Gly
             140             145                150
Ser Ala Lys Pro Gly Leu Gln Lys Val Val Asp Val Leu Asp Ser
             155             160                165
Ile Lys Thr Lys Gly Lys Ser Ala Asp Phe Thr Asn Phe Asp Pro
             170             175                180
Arg Gly Leu Leu Pro Glu Ser Leu Asp Tyr Trp Thr Tyr Pro Gly
             185             190                195
Ser Leu Thr Thr Pro Pro Leu Leu Glu Cys Val Thr Trp Ile Val
             200             205                210
Leu Lys Glu Pro Ile Ser Val Ser Ser Glu Gln Val Leu Lys Phe
             215             220                225
Arg Lys Leu Asn Phe Asn Gly Glu Gly Glu Pro Glu Glu Leu Met
             230             235                240
Val Asp Asn Trp Arg Pro Ala Gln Pro Leu Lys Asn Arg Gln Ile
             245             250                255
Lys Ala Ser Phe Lys
             260
```

FIGURE 8 (SEQ ID NO 3)

```
Met Ser His His Trp Gly Tyr Gly Lys His Asn Gly Pro Glu His
                5                   10                  15

Trp His Lys Asp Phe Pro Ile Ala Lys Gly Glu Arg Gln Ser Pro
                20                  25                  30

Val Asp Ile Asp Thr His Thr Ala Lys Tyr Asp Pro Ser Leu Lys
                35                  40                  45

Pro Leu Ser Val Ser Tyr Asp Gln Ala Thr Ser Leu Arg Ile Leu
                50                  55                  60

Asn Asn Gly His Ala Phe Asn Val Glu Phe Asp Asp Ser Gln Asp
                65                  70                  75

Lys Ala Val Leu Lys Gly Gly Pro Leu Asp Gly Thr Tyr Arg Leu
                80                  85                  90

Ile Gln Leu His Phe His Trp Gly Ser Leu Asp Gly Gln Gly Ser
                95                  100                 105

Glu His Thr Val Asp Lys Lys Tyr Ala Ala Glu Leu His Leu
                110                 115                 120

Val His Trp Asn Thr Lys Tyr Gly Asp Phe Gly Lys Ala Val Gln
                125                 130                 135

Gln Pro Asp Gly Leu Ala Val Leu Gly Ile Phe Leu Lys Val Gly
                140                 145                 150

Ser Ala Lys Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260
```

FIGURE 9 (SEQ ID NO 4)

```
Met Ser His His Trp Gly Tyr Gly Lys His Asn Gly Pro Glu His
                    5                   10                  15

Trp His Lys Asp Phe Pro Ile Ala Lys Gly Glu Arg Gln Ser Pro
                20                  25                  30

Val Asp Ile Asp Thr His Thr Ala Lys Tyr Asp Pro Ser Leu Lys
                35                  40                  45

Pro Leu Ser Val Ser Tyr Asp Gln Ala Thr Ser Leu Arg Ile Leu
                50                  55                  60

Asn Asn Gly His Ala Phe Asn Val Glu Phe Asp Asp Ser Gln Asp
                65                  70                  75

Lys Ala Val Leu Lys Gly Gly Pro Leu Asp Gly Thr Tyr Arg Leu
                80                  85                  90

Ile Gln Phe His Phe His Trp Gly Ser His Asp Gly Gln Gly Ser
                95                  100                 105

Glu His Thr Val Asp Lys Lys Tyr Ala Ala Glu Leu His Leu
                110                 115                 120

Val His Trp Asn Thr Lys Tyr Gly Asp Phe Gly Lys Ala Val Gln
                125                 130                 135

Gln Pro Asp Gly Leu Ala Val Leu Gly Ile Phe Leu Lys Val Gly
                140                 145                 150

Ser Ala Lys Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260
```

FIGURE 10 (SEQ ID NO 5)

```
Met Ser His His Trp Gly Tyr Gly Lys His Asn Gly Pro Glu His
             5                   10                      15

Trp His Lys Asp Phe Pro Ile Ala Lys Gly Glu Arg Gln Ser Pro
            20                   25                      30

Val Asp Ile Asp Thr His Thr Ala Lys Tyr Asp Pro Ser Leu Lys
            35                   40                      45

Pro Leu Ser Val Ser Tyr Asp Gln Ala Thr Ser Leu Arg Ile Leu
            50                   55                      60

Asn Asn Gly His Ala Phe Asn Val Glu Phe Asp Asp Ser Gln Asp
            65                   70                      75

Lys Ala Val Leu Lys Gly Gly Pro Leu Asp Gly Thr Tyr Arg Leu
            80                   85                      90

Ile Gln Phe His Phe His Trp Gly Ser Leu Asp Gly Gln Gly Ser
            95                  100                     105

Glu His Thr Val Asp Lys Lys Tyr Ala Ala Glu Leu His Leu
           110                  115                     120

Val His Trp Asn Thr Lys Tyr Gly Asp Phe Gly Lys Ala Val Gln
           125                  130                     135

Tyr Pro Asp Gly Leu Ala Val Leu Gly Ile Phe Leu Lys Val Gly
           140                  145                     150

Ser Ala Lys Pro Gly Leu Gln Lys Val Val Asp Val Leu Asp Ser
           155                  160                     165

Ile Lys Thr Lys Gly Lys Ser Ala Asp Phe Thr Asn Phe Asp Pro
           170                  175                     180

Arg Gly Leu Leu Pro Glu Ser Leu Asp Tyr Trp Thr Tyr Pro Gly
           185                  190                     195

Ser Leu Thr Thr Pro Pro Leu Leu Glu Cys Val Thr Trp Ile Val
           200                  205                     210

Leu Lys Glu Pro Ile Ser Val Ser Ser Glu Gln Val Leu Lys Phe
           215                  220                     225

Arg Lys Leu Asn Phe Asn Gly Glu Gly Glu Pro Glu Glu Leu Met
           230                  235                     240

Val Asp Asn Trp Arg Pro Ala Gln Pro Leu Lys Asn Arg Gln Ile
           245                  250                     255

Lys Ala Ser Phe Lys
           260
```

FIGURE 11 (SEQ ID NO 6)

```
Met Ser His His Trp Gly Tyr Gly Lys His Asn Gly Pro Glu His
             5                  10                      15

Trp His Lys Asp Phe Pro Ile Ala Lys Gly Glu Arg Gln Ser Pro
             20                 25                      30

Val Asp Ile Asp Thr His Thr Ala Lys Tyr Asp Pro Ser Leu Lys
             35                 40                      45

Pro Leu Ser Val Ser Tyr Asp Gln Ala Thr Ser Leu Arg Ile Leu
             50                 55                      60

Asn Asn Gly His Ala Phe Asn Val Glu Phe Asp Asp Ser Gln Asp
             65                 70                      75

Lys Ala Val Leu Lys Gly Gly Pro Leu Asp Gly Thr Tyr Arg Leu
             80                 85                      90

Ile Gln Phe His Phe His Trp Gly Ser Leu Asp Gly Gln Gly Ser
             95                 100                     105

Glu His Thr Val Asp Lys Lys Tyr Ala Ala Glu Leu His Leu
             110                115                     120

Val His Trp Asn Thr Lys Tyr Gly Asp Phe Gly Lys Ala Val Gln
             125                130                     135

His Pro Asp Gly Leu Ala Val Leu Gly Ile Phe Leu Lys Val Gly
             140                145                     150

Ser Ala Lys Pro Gly Leu Gln Lys Val Val Asp Val Leu Asp Ser
             155                160                     165

Ile Lys Thr Lys Gly Lys Ser Ala Asp Phe Thr Asn Phe Asp Pro
             170                175                     180

Arg Gly Leu Leu Pro Glu Ser Leu Asp Tyr Trp Thr Tyr Pro Gly
             185                190                     195

Ser Leu Thr Thr Pro Pro Leu Leu Glu Cys Val Thr Trp Ile Val
             200                205                     210

Leu Lys Glu Pro Ile Ser Val Ser Ser Glu Gln Val Leu Lys Phe
             215                220                     225

Arg Lys Leu Asn Phe Asn Gly Glu Gly Glu Pro Glu Glu Leu Met
             230                235                     240

Val Asp Asn Trp Arg Pro Ala Gln Pro Leu Lys Asn Arg Gln Ile
             245                250                     255

Lys Ala Ser Phe Lys
             260
```

FIGURE 12 (SEQ ID NO 7)

| | | | | | | | | | | | | | | |
|---|---|---|---|---|---|---|---|---|---|---|---|---|---|---|
| Met | Ser | His | His | Trp | Gly | Tyr | Gly | Lys | His | Asn | Gly | Pro | Glu | His |
| | | | | 5 | | | | | 10 | | | | | 15 |
| Trp | His | Lys | Asp | Phe | Pro | Ile | Ala | Lys | Gly | Glu | Arg | Gln | Ser | Pro |
| | | | | 20 | | | | | 25 | | | | | 30 |
| Val | Asp | Ile | Asp | Thr | His | Thr | Ala | Lys | Tyr | Asp | Pro | Ser | Leu | Lys |
| | | | | 35 | | | | | 40 | | | | | 45 |
| Pro | Leu | Ser | Val | Ser | Tyr | Asp | Gln | Ala | Thr | Ser | Leu | Arg | Ile | Leu |
| | | | | 50 | | | | | 55 | | | | | 60 |
| Asn | Asn | Gly | His | Ala | Phe | Asn | Val | Glu | Phe | Asp | Asp | Ser | Gln | Asp |
| | | | | 65 | | | | | 70 | | | | | 75 |
| Lys | Ala | Val | Leu | Lys | Gly | Gly | Pro | Leu | Asp | Gly | Thr | Tyr | Arg | Leu |
| | | | | 80 | | | | | 85 | | | | | 90 |
| Ile | Gln | Phe | His | Phe | His | Trp | Gly | Ser | Leu | Asp | Gly | Gln | Gly | Ser |
| | | | | 95 | | | | | 100 | | | | | 105 |
| Glu | His | Thr | Val | Asp | Lys | Lys | Tyr | Ala | Ala | Glu | Leu | His | Leu |
| | | | | 110 | | | | | 115 | | | | | 120 |
| Val | His | Trp | Asn | Thr | Lys | Tyr | Gly | Asp | Phe | Gly | Lys | Ala | Val | Gln |
| | | | | 125 | | | | | 130 | | | | | 135 |
| Gln | Pro | Asp | Gly | Leu | Ala | Val | Leu | Gly | Ile | Phe | Leu | Lys | Val | Gly |
| | | | | 140 | | | | | 145 | | | | | 150 |
| Ser | Ala | Leu | Pro | Gly | Leu | Gln | Lys | Val | Val | Asp | Val | Leu | Asp | Ser |
| | | | | 155 | | | | | 160 | | | | | 165 |
| Ile | Lys | Thr | Lys | Gly | Lys | Ser | Ala | Asp | Phe | Thr | Asn | Phe | Asp | Pro |
| | | | | 170 | | | | | 175 | | | | | 180 |
| Arg | Gly | Leu | Leu | Pro | Glu | Ser | Leu | Asp | Tyr | Trp | Thr | Tyr | Pro | Gly |
| | | | | 185 | | | | | 190 | | | | | 195 |
| Ser | Leu | Thr | Thr | Pro | Pro | Leu | Leu | Glu | Cys | Val | Thr | Trp | Ile | Val |
| | | | | 200 | | | | | 205 | | | | | 210 |
| Leu | Lys | Glu | Pro | Ile | Ser | Val | Ser | Ser | Glu | Gln | Val | Leu | Lys | Phe |
| | | | | 215 | | | | | 220 | | | | | 225 |
| Arg | Lys | Leu | Asn | Phe | Asn | Gly | Glu | Gly | Glu | Pro | Glu | Glu | Leu | Met |
| | | | | 230 | | | | | 235 | | | | | 240 |
| Val | Asp | Asn | Trp | Arg | Pro | Ala | Gln | Pro | Leu | Lys | Asn | Arg | Gln | Ile |
| | | | | 245 | | | | | 250 | | | | | 255 |
| Lys | Ala | Ser | Phe | Lys | | | | | | | | | | |
| | | | | 260 | | | | | | | | | | |

FIGURE 13 (SEQ ID NO 8)

```
Met Ser His His Trp Gly Tyr Gly Lys His Asn Gly Pro Glu His
            5                   10                  15

Trp His Lys Asp Phe Pro Ile Ala Lys Gly Glu Arg Gln Ser Pro
            20                  25                  30

Val Asp Ile Asp Thr His Thr Ala Lys Tyr Asp Pro Ser Leu Lys
            35                  40                  45

Pro Leu Ser Val Ser Tyr Asp Gln Ala Thr Ser Leu Arg Ile Leu
            50                  55                  60

Asn Asn Gly His Ala Phe Asn Val Glu Phe Asp Asp Ser Gln Asp
            65                  70                  75

Lys Ala Val Leu Lys Gly Gly Pro Leu Asp Gly Thr Tyr Arg Leu
            80                  85                  90

Ile Gln Phe His His Trp Gly Ser Leu Asp Gly Gln Gly Ser
            95                  100                 105

Glu His Thr Val Asp Lys Lys Tyr Ala Ala Glu Leu His Leu
            110                 115                 120

Val His Trp Asn Thr Lys Tyr Gly Asp Phe Gly Lys Ala Val Gln
            125                 130                 135

Gln Pro Asp Gly Leu Ala Val Leu Gly Ile Phe Leu Lys Val Gly
            140                 145                 150

Ser Ala Lys Pro Gly Leu Gln Lys Val Val Asp Val Leu Asp Ser
            155                 160                 165

Ile Lys Thr Lys Gly Lys Ser Ala Asp Phe Thr Asn Phe Asp Pro
            170                 175                 180

Arg Gly Leu Leu Pro Glu Ser Leu Asp Tyr Trp Thr Tyr Pro Gly
            185                 190                 195

Ser Met Thr Thr Pro Pro Leu Leu Glu Cys Val Thr Trp Ile Val
            200                 205                 210

Leu Lys Glu Pro Ile Ser Val Ser Ser Glu Gln Val Leu Lys Phe
            215                 220                 225

Arg Lys Leu Asn Phe Asn Gly Glu Gly Glu Pro Glu Glu Leu Met
            230                 235                 240

Val Asp Asn Trp Arg Pro Ala Gln Pro Leu Lys Asn Arg Gln Ile
            245                 250                 255

Lys Ala Ser Phe Lys
            260
```

FIGURE 14 (SEQ ID NO 9)

```
Met Ser His His Trp Gly Tyr Gly Lys His Asn Gly Pro Glu His
                  5                  10                  15

Trp His Lys Asp Phe Pro Ile Ala Lys Gly Glu Arg Gln Ser Pro
                 20                  25                  30

Val Asp Ile Asp Thr His Thr Ala Lys Tyr Asp Pro Ser Leu Lys
                 35                  40                  45

Pro Leu Ser Val Ser Tyr Asp Gln Ala Thr Ser Leu Arg Ile Leu
                 50                  55                  60

Asn Asn Gly His Ala Phe Asn Val Glu Phe Asp Asp Ser Gln Asp
                 65                  70                  75

Lys Ala Val Leu Lys Gly Gly Pro Leu Asp Gly Thr Tyr Arg Leu
                 80                  85                  90

Ile Gln Phe His Phe His Trp Gly Ser Leu Asp Gly Gln Gly Ser
                 95                 100                 105

Glu His Thr Val Asp Lys Lys Tyr Ala Ala Glu Leu His Leu
                110                 115                 120

Val His Trp Asn Thr Lys Tyr Gly Asp Phe Gly Lys Ala Val Gln
                125                 130                 135

Gln Pro Asp Gly Leu Ala Val Leu Gly Ile Phe Leu Lys Val Gly
                140                 145                 150

Ser Ala Lys Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Ser Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260
```

FIGURE 15 (SEQ ID NO 10)

```
Met Ser His His Trp Gly Tyr Gly Lys His Asn Gly Pro Glu His
             5                  10                 15

Trp His Lys Asp Phe Pro Ile Ala Lys Gly Glu Arg Gln Ser Pro
             20                 25                 30

Val Asp Ile Asp Thr His Thr Ala Lys Tyr Asp Pro Ser Leu Lys
             35                 40                 45

Pro Leu Ser Val Ser Tyr Asp Gln Ala Thr Ser Leu Arg Ile Leu
             50                 55                 60

Asn Asn Gly His Ala Phe Asn Val Glu Phe Asp Asp Ser Gln Asp
             65                 70                 75

Lys Ala Val Leu Lys Gly Gly Pro Leu Asp Gly Thr Tyr Arg Leu
             80                 85                 90

Ile Gln Phe His Phe His Trp Gly Ser Leu Asp Gly Gln Gly Ser
             95                 100                105

Glu His Thr Val Asp Lys Lys Tyr Ala Ala Glu Leu His Leu
             110                115                120

Val His Trp Asn Thr Lys Tyr Gly Asp Phe Gly Lys Ala Val Gln
             125                130                135

Gln Pro Asp Gly Leu Ala Val Leu Gly Ile Phe Leu Lys Val Gly
             140                145                150

Ser Ala Lys Pro Gly Leu Gln Lys Val Val Asp Val Leu Asp Ser
             155                160                165

Ile Lys Thr Lys Gly Lys Ser Ala Asp Phe Thr Asn Phe Asp Pro
             170                175                180

Arg Gly Leu Leu Pro Glu Ser Leu Asp Tyr Trp Thr Tyr Pro Gly
             185                190                195

Ser Leu Thr Thr Pro Pro Leu Leu Glu Cys Val Thr Trp Ile Val
             200                205                210

Leu Lys Glu Pro Ile Ser Val Ser Ser Glu Gln Val Leu Lys Phe
             215                220                225

Arg Lys Leu Asn Phe Asn Gly Glu Gly Glu Pro Glu Glu Pro Met
             230                235                240

Val Asp Asn Trp Arg Pro Ala Gln Pro Leu Lys Asn Arg Gln Ile
             245                250                255

Lys Ala Ser Phe Lys
             260
```

FIGURE 16 (SEQ ID NO 11)

```
Met Ser His His Trp Gly Tyr Gly Lys His Asn Gly Pro Glu His
             5                  10                      15

Trp His Lys Asp Phe Pro Ile Ala Lys Gly Glu Arg Gln Ser Pro
             20                  25                      30

Val Asp Ile Asp Thr His Thr Ala Lys Tyr Asp Pro Ser Leu Lys
             35                  40                      45

Pro Leu Ser Val Ser Tyr Asp Gln Ala Thr Ser Leu Arg Ile Leu
             50                  55                      60

Asn Asn Gly His Ala Phe Asn Val Glu Phe Asp Asp Ser Gln Asp
             65                  70                      75

Lys Ala Val Leu Lys Gly Gly Pro Leu Asp Gly Thr Tyr Arg Leu
             80                  85                      90

Ile Gln Phe His Phe His Trp Gly Ser Leu Asp Gly Gln Gly Ser
             95                  100                     105

Glu His Thr Val Asp Lys Lys Tyr Ala Ala Glu Leu His Leu
             110                 115                     120

Val His Trp Asn Thr Lys Tyr Gly Asp Phe Gly Lys Ala Val Gln
             125                 130                     135

Gln Pro Asp Gly Leu Ala Val Leu Gly Ile Phe Leu Lys Val Gly
             140                 145                     150

Ser Ala Lys Pro Gly Leu Gln Lys Val Val Asp Val Leu Asp Ser
             155                 160                     165

Ile Lys Thr Lys Gly Lys Ser Ala Asp Phe Thr Asn Phe Asp Pro
             170                 175                     180

Arg Gly Leu Leu Pro Glu Ser Leu Asp Tyr Trp Thr Tyr Pro Gly
             185                 190                     195

Ser Leu Thr Thr Pro Pro Leu Leu Glu Cys Val Thr Trp Ile Val
             200                 205                     210

Leu Lys Glu Pro Ile Ser Val Ser Ser Glu Gln Val Leu Lys Phe
             215                 220                     225

Arg Lys Leu Asn Phe Asn Gly Glu Gly Glu Pro Glu Glu Leu Met
             230                 235                     240

Val Asp Asn Trp Arg Pro Thr Gln Pro Leu Lys Asn Arg Gln Ile
             245                 250                     255

Lys Ala Ser Phe Lys
             260
```

FIGURE 17 (SEQ ID NO 12)

```
atgtcccatc actgggggta cggcaaacac aacggacctg agcactggca taaggacttc    60
cccattgcca agggagagcg ccagtccct gttgacatcg acactcatac agccaagtat   120
gacccttccc tgaagcccct gtctgtttcc tatgatcaag caacttccct gaggatcctc   180
aacaatggtc atactttcaa cgtggagttt gatgactctc aggacaaagc agtgctcaag   240
ggaggacccc tggatggcac ttacagattg attcagtttc actttcactg gggttcactt   300
gatggacaag gttcagagca tactgtggat aaaaagaaat atgctgcaga acttcacttg   360
gttcactgga acaccaaata tggggatttt gggaaagctg tgcagcaacc tgatggactg   420
gccgttctag gtattttttt gaaggttggc agcgctaaac cgggccttca gaaagttgtt   480
gatgtgctgg attccattaa aacaaagggc aagagtgctg acttcactaa cttcgatcct   540
cgtggcctcc ttcctgaatc cctggattac tggacctacc caggctcact gaccacccct   600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                  783
```

FIGURE 18 (SEQ ID NO 13)

```
atgtcccatc actgggggta cggcaaacac aacggacctg agcactggca taaggacttc    60
cccattgcca agggagagcg ccagtccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagttgc actttcactg gggttcactt   300
gatggacaag gttcagagca tactgtggat aaaaagaaat atgctgcaga acttcacttg   360
gttcactgga acaccaaata tggggatttt gggaaagctg tgcagcaacc tgatggactg   420
gccgttctag gtattttttt gaaggttggc agcgctaaac cgggccttca gaaagttgtt   480
gatgtgctgg attccattaa aacaaagggc aagagtgctg acttcactaa cttcgatcct   540
cgtggcctcc ttcctgaatc cctggattac tggacctacc caggctcact gaccacccct   600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                  783
```

FIGURE 19 (SEQ ID NO 14)

```
atgtcccatc actgggggta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttcacat   300
gatggacaag gttcagagca tactgtggat aaaagaaat atgctgcaga acttcacttg    360
gttcactgga acaccaaata tggggatttt gggaaagctg tgcagcaacc tgatggactg   420
gccgttctag gtattttttt gaaggttggc agcgctaaac cgggccttca gaaagttgtt   480
gatgtgctgg attccattaa aacaaagggc aagagtgctg acttcactaa cttcgatcct   540
cgtggcctcc ttcctgaatc cctggattac tggacctacc caggctcact gaccacccct   600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                 783
```

FIGURE 20 (SEQ ID NO 15)

```
atgtcccatc actgggggta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttcactt   300
gatggacaag gttcagagca tactgtggat aaaagaaat atgctgcaga acttcacttg    360
gttcactgga acaccaaata tggggatttt gggaaagctg tgcagtatcc tgatggactg   420
gccgttctag gtattttttt gaaggttggc agcgctaaac cgggccttca gaaagttgtt   480
gatgtgctgg attccattaa aacaaagggc aagagtgctg acttcactaa cttcgatcct   540
cgtggcctcc ttcctgaatc cctggattac tggacctacc caggctcact gaccacccct   600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                 783
```

FIGURE 21 (SEQ ID NO 16)

```
atgtcccatc actggggta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttcactt   300
gatggacaag gttcagagca tactgtggat aaaaagaaat atgctgcaga acttcacttg   360
gttcactgga acaccaaata tggggatttt gggaaagctg tgcagcatcc tgatggactg   420
gccgttctag gtattttttt gaaggttggc agcgctaaac cgggccttca gaaagttgtt   480
gatgtgctgg attccattaa aacaaagggc aagagtgctg acttcactaa cttcgatcct   540
cgtggcctcc ttcctgaatc cctggattac tggacctacc aggctcact gaccacccct    600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                 783
```

FIGURE 22 (SEQ ID NO 17)

```
atgtcccatc actggggta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttcactt   300
gatggacaag gttcagagca tactgtggat aaaaagaaat atgctgcaga acttcacttg   360
gttcactgga acaccaaata tggggatttt gggaaagctg tgcagcaacc tgatggactg   420
gccgttctag gtattttttt gaaggttggc agcgctctac cgggccttca gaaagttgtt   480
gatgtgctgg attccattaa aacaaagggc aagagtgctg acttcactaa cttcgatcct   540
cgtggcctcc ttcctgaatc cctggattac tggacctacc aggctcact gaccacccct    600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                 783
```

FIGURE 23 (SEQ ID NO 18)

```
atgtcccatc actggggtta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttcactt   300
gatggacaag gttcagagca tactgtggat aaaaagaaat atgctgcaga acttcacttg   360
gttcactgga acaccaaata tggggatttt gggaaagctg tgcagcaacc tgatggactg   420
gccgttctag gtattttttt gaaggttggc agcgctaaac cgggccttca gaaagttgtt   480
gatgcgctgg attccattaa aacaaagggc aagagtgctg acttcactaa cttcgatcct   540
cgtggcctcc ttcctgaatc cctggattac tggacctacc caggctcact gaccacccct   600
cctcttctgg aatgtgtgac ctggattgtg ctcaaggaac ccatcagcgt cagcagcgag   660
caggtgttga aattccgtaa acttaacttc aatggggagg gtgaacccga agaactgatg   720
gtggacaact ggcgcccagc tcagccactg aagaacaggc aaatcaaagc ttccttcaaa   780
taa                                                                783
```

FIGURE 24 (SEQ ID NO 19)

```
atgtcccatc actggggtta cggcaaacac aacggacctg agcactggca taaggacttc    60
cccattgcca agggagagcg ccagtcccct gttgacatcg acactcatac agccaagtat   120
gacccttccc tgaagcccct gtctgtttcc tatgatcaag caacttccct gaggatcctc   180
aacaatggtc atgctttcaa cgtggagttt gatgactctc aggacaaagc agtgctcaag   240
ggaggacccc tggatggcac ttacagattg attcagtttc actttcactg gggttcactt   300
gatggacaag gttcagagca tactgtggat aaaaagaaat atgctgcaga acttcacttg   360
gttcactgga acaccaaata tggggatttt gggaaagctg tgcagcaacc tgatggactg   420
gccgttctag gtattttttt gaaggttggc agcgctaaac cgggccttca gaaagttgtt   480
gatgtgctgg attccattaa aacaaagggc aagagtgctg acttcactaa cttcgatcct   540
cgtggcctcc ttcctgaatc cctggattac tggacctacc caggctcact gaccacccct   600
cctcttctgg aatgtgtgac ctggattgtg ctcaaggaac ccatcagcgt cagcagcgag   660
caggtgtcga aattccgtaa acttaacttc aatggggagg gtgaacccga agaactgatg   720
gtggacaact ggcgcccagc tcagccactg aagaacaggc aaatcaaagc ttccttcaaa   780
taa                                                                783
```

FIGURE 25 (SEQ ID NO 20)

```
atgtcccatc actgggggta cggcaaacac aacggacctg agcactggca taaggacttc    60
cccattgcca agggagagcg ccagtccct gttgacatcg acactcatac agccaagtat    120
gacccttccc tgaagcccct gtctgtttcc tatgatcaag caacttccct gaggatcctc    180
aacaatggtc atgctttcaa cgtggagttt gatgactctc aggacaaagc agtgctcaag    240
ggaggacccc tggatggcac ttacagattg attcagtttc actttcactg gggttcactt    300
gatggacaag gttcagagca tactgtggat aaaaagaaat atgctgcaga acttcacttg    360
gttcactgga acaccaaata tggggatttt gggaagctg tgcagcaacc tgatggactg     420
gccgttctag gtatttttt gaaggttggc agcgctaaac cgggccttca gaaagttgtt    480
gatgtgctgg attccattaa aacaaaggc aagagtgctg acttcactaa cttcgatcct    540
cgtggcctcc ttcctgaatc cctggattac tggacctacc caggctcact gaccacccct    600
cctcttctgg aatgtgtgac ctggattgtg ctcaaggaac ccatcagcgt cagcagcgag    660
caggtgttga aattccgtaa acttaacttc aatggggagg gtgaacccga agaaccgatg    720
gtggacaact ggcgcccagc tcagccactg aagaacaggc aaatcaaagc ttccttcaaa    780
taa                                                                  783
```

FIGURE 26 (SEQ ID NO 21)

```
atgtcccatc actgggggta cggcaaacac aacggacctg agcactggca taaggacttc    60
cccattgcca agggagagcg ccagtccct gttgacatcg acactcatac agccaagtat    120
gacccttccc tgaagcccct gtctgtttcc tatgatcaag caacttccct gaggatcctc    180
aacaatggtc atgctttcaa cgtggagttt gatgactctc aggacaaagc agtgctcaag    240
ggaggacccc tggatggcac ttacagattg attcagtttc actttcactg gggttcactt    300
gatggacaag gttcagagca tactgtggat aaaaagaaat atgctgcaga acttcacttg    360
gttcactgga acaccaaata tggggatttt gggaagctg tgcagcaacc tgatggactg     420
gccgttctag gtatttttt gaaggttggc agcgctaaac cgggccttca gaaagttgtt    480
gatgtgctgg attccattaa aacaaaggc aagagtgctg acttcactaa cttcgatcct    540
cgtggcctcc ttcctgaatc cctggattac tggacctacc caggctcact gaccacccct    600
cctcttctgg aatgtgtgac ctggattgtg ctcaaggaac ccatcagcgt cagcagcgag    660
caggtgttga aattccgtaa acttaacttc aatggggagg gtgaacccga agaactgatg    720
gtggacaact ggcgcccaac tcagccactg aagaacaggc aaatcaaagc ttccttcaaa    780
taa                                                                  783
```

CARBONIC ANHYDRASE HAVING INCREASED STABILITY UNDER HIGH TEMPERATURE CONDITIONS

CROSS-REFERENCE TO RELATED APPLICATIONS

This application claims priority under 35 U.S.C. § 119(e) to U.S. Provisional Application No. 60/673,345 filed on Apr. 21, 2005.

FIELD OF THE INVENTION

The present invention relates to polynucleotide and polypeptide sequences of novel carbonic anhydrase variants having increased stability under high temperature conditions compared to native carbonic anhydrase.

BRIEF DESCRIPTION OF THE PRIOR ART

Carbonic anhydrase (EC 4.2.1.1.) is a globular zinc metalloenzyme of molecular weight 30,000 daltons. The enzyme was discovered in 1933 and has been the subject of intense scientific investigation. Multiple isoforms have been discovered in plant and animal tissues where it is believed to facilitate the transport of carbon dioxide. Red blood cells contain isoenzymes I and II, which are the most active. Carbonic anhydrase II has the highest molecular turnover number of any known enzyme. One molecule of carbonic anhydrase can hydrate 36,000,000 molecules of carbon dioxide in a period of 60 seconds. Physiologically, carbonic anhydrase facilitates the removal of carbon dioxide from the mammalian body. The general enzyme reaction is shown below.

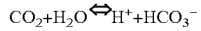

$$CO_2 + H_2O \rightleftharpoons H^+ + HCO_3^-$$

Human carbonic anhydrase II (CAII) variants have also been the subject of scientific investigation. Indeed, the functional importance of a conserved hydrophobic face in human carbonic anhydrase II (CAII), including amino acid residues 190-210, was investigated by random mutagenesis.[1]

Other CAII variants have been obtained by substituting amino acids of varying size at position 65, for instance by changing the amino acid Ala for the amino acid Thr. This modification was done in order to investigate the importance of maintaining the active site water network for efficient proton transfer.[2,3]

A library of CAII variants differing in hydrophobic amino acid residues Phe93, Phe95, and Trp97 was also prepared using cassette mutagenesis, then displayed on filamentous phage, and screened for proteins retaining high zinc affinity.[4]

It exists a need in the art for the development of innovative carbonic anhydrase variants harboring advantageous characteristics over native carbonic anhydrases, such as exhibiting increased stability under high temperature conditions.

BRIEF DESCRIPTION OF THE FIGURES

FIG. 6 shows the amino acid sequence of the native unmodified carbonic anhydrase II (SEQ ID NO: 1).

FIGS. 7 to 16 show the amino acid sequence of modified carbonic anhydrases according to preferred embodiments of the invention (SEQ ID NOS: 2 to 11).

FIGS. 17 to 26 show the nucleotide sequence encoding the carbonic anhydrases of FIGS. 7 to 12 (SEQ ID NOS: 12 to 21).

DETAILED DESCRIPTION OF THE INVENTION

Figure 1:
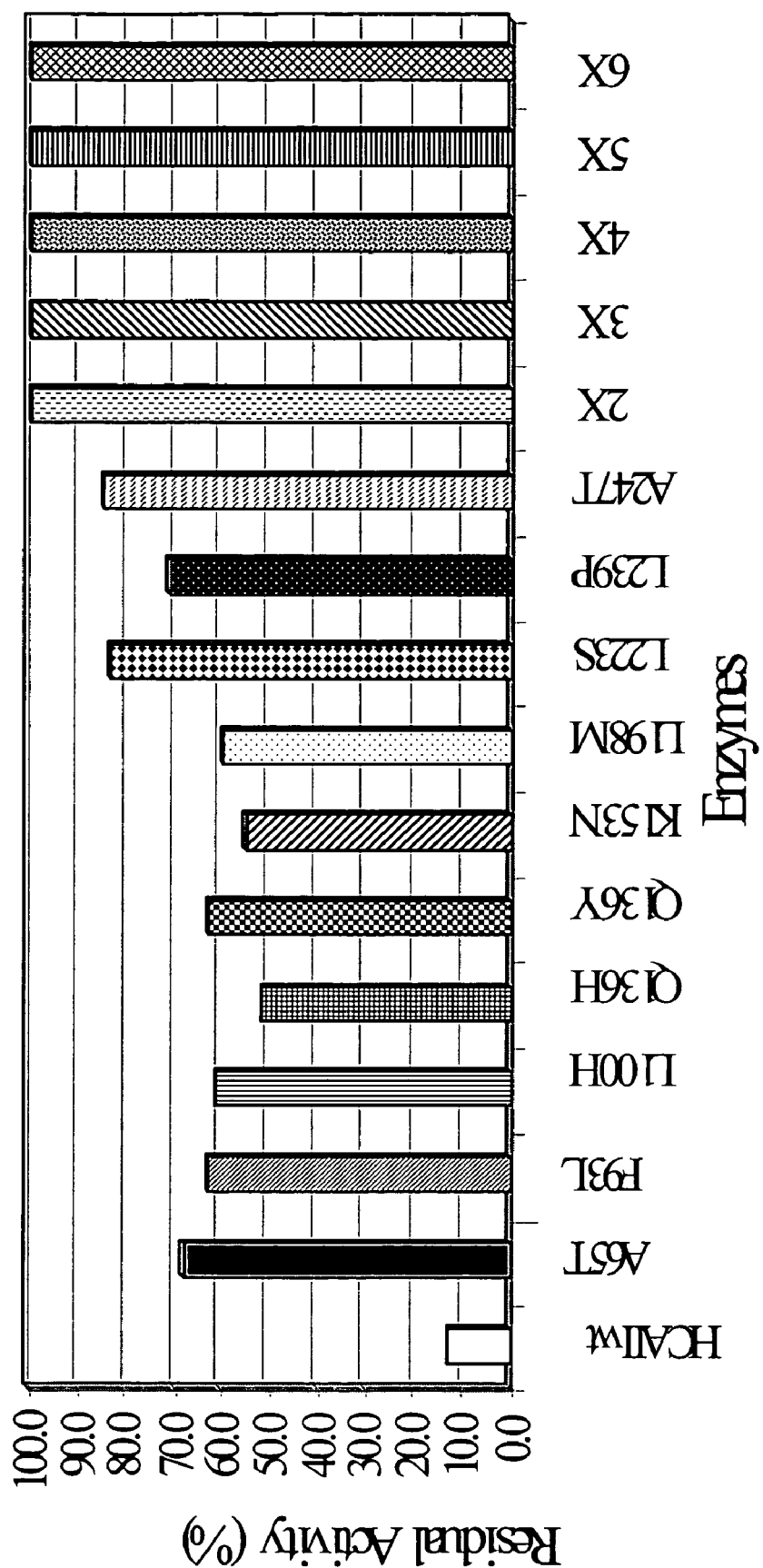
FIG. 1 shows the residual enzymatic activity of modified carbonic anhydrases II according to preferred embodiments of the invention following a 2 hour treatment at 55° C.

The inventors have surprisingly found that a number of mutations of human carbonic anhydrase II (HCAII), individually or in combination, provide a stabilizing effect on the modified HCAII protein and enable enzymatic activity at higher temperature than normal (i.e higher than 25° C.). In this connection, the present invention specifically relates to the identification of polypeptides and polynucleotide sequences encoding a modified carbonic anhydrase (CA), preferably of human origin, which have increased stability compared to native CA.

1. Definitions

In describing the present invention, the following terms will be employed, and are intended to be defined as indicated below.

As used herein, the expression "high temperature conditions" refers to temperature higher than 25° C. and lower than 70° C. Preferably, it refers to temperature higher than about 37° C., more preferably higher than about 55° C. and even more preferably higher than about 65° C. By "about", it is meant that the value of said temperature can vary within a certain range depending on the margin of error of the method or apparatus used to evaluate such temperature. For instance, the margin of error may range between ±1° C. to ±5° C.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide.

A "functional derivative", as is generally understood and used herein, refers to a protein/peptide/polypeptide sequence that possesses a functional biological activity that is substantially similar to the biological activity of the whole protein/peptide/polypeptide sequence. In other words, it refers to a polypeptide of a modified CA of the invention that substantially retain(s) the capacity of catalyzing the hydration of carbon dioxide. A functional derivative of a modified CA protein/peptide of the invention may or may not contain post-translational modifications such as covalently linked carbohydrates, if such modification is not necessary for the performance of a specific function. The term "functional derivative" is meant to encompass the "fragments" or "chemical derivatives" of a modified CA protein/peptide of the invention. As used herein, a protein/peptide is said to be a "chemical derivative" of a modified CA protein/peptide of the invention when it contains additional chemical moieties not normally part of the protein/peptide, said moieties being added by using techniques well known in the art.

By "substantially identical" when refering to a polypeptide, it will be understood that the polypeptide of the present invention preferably has an amino acid sequence having at least 80% identity, or even preferably 85% identity, or even more preferably 95% to SEQ ID NOS:1 to 11, or functional derivatives thereof.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTp will align the longest stretch of similar sequences and assign a value to the fit. It is thus possible to obtain a comparison where several regions of similarity are found, each having a different score. Both types of identity analysis are contemplated by the present invention.

With respect to protein or polypeptide, the term "isolated polypeptide" or "isolated and purified polypeptide" is sometimes used herein. This term refers primarily to a protein produced by expression of an isolated and modified polynucleotide molecule contemplated by the invention. Alternatively, this term may refer to a protein which has been sufficiently separated from other proteins with which it would naturally be associated, so as to exist in "substantially pure" form.

The term "substantially pure" refers to a preparation comprising at least 50-60% by weight of the modified CA polypeptide of the invention. More preferably, the preparation comprises at least 75% by weight, and most preferably 90-99% by weight, of the modified CA polypeptide of the invention.

Purity is measured by methods appropriate for the modified CA polypeptide of the invention (e.g. chromatographic methods, agarose or polyacrylamide gel electrophoresis, HPLC analysis, and the like).

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides", that due to mutagenesis are not 100% identical but nevertheless code for the same amino acid sequence.

By "substantially identical" when referring to a polynucleotide, it will be understood that the polynucleotide of the invention has a nucleic acid sequence which is at least 65% identical, more particularly 80% identical and even more particularly 95% identical to any one of SEQ ID NO 12 to 21 or functional fragments thereof.

A "functional fragment", as is generally understood and used herein, refers to a nucleic acid sequence that encodes for a functional biological activity of protein that is substantially similar to the biological activity of protein coding of the whole nucleic acid sequence. In other words, it refers to a nucleic acid or fragment(s) thereof that substantially retains the capacity of encoding a carbonic anhydrase polypeptide of the invention.

The term "fragment", as used herein, refers to a polynucleotide sequence (e.g., cDNA) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the invention, the term "isolated polynucleotide" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated polynucleotide" may comprise a DNA molecule inserted into a vector, such as a plasmid or virus vector, or integrated into the genomic DNA of a procaryote or eucaryote. An "isolated polynucleotide molecule" may also comprise a cDNA molecule.

Amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B", it is meant that n % of the positions of an optimal global alignment between sequences A and B consists of identical residues or nucleotides and conservative substitutions. By the statement "sequence A is n % identical to sequence B", it is meant that n % of the positions of an optimal global alignment between sequences A and B consists of identical residues or nucleotides.

2. Modified CA Polynucleotides and Polypeptides of the Invention

In a first embodiment, the present invention concerns a modified carbonic anhydrase polypeptide having increased stability under high temperature conditions compared to unmodified carbonic anhydrase, i.e. a modified CA that satisfactory retains enzymatic activity at a temperature higher than suitable for use with native CA (for instance higher than about 25° C.). As used herein, the term "modified CA" refers to forms of CA that differ structurally from unmodified CA. In particular, the modified CA protein of the invention comprise an amino acid sequence substantially identical to SEQ ID NO 1 and wherein the modified CA comprises at least one amino acid substitution at a position, or at an equivalent position, corresponding to position 65, 93, 100, 136, 153, 198, 223, 239 and 247 of SEQ ID NO 1. In this connection, the term "equivalent position" denotes a position which, on the basis of an alignment of the amino acid sequence of the parent carbonic anhydrase in question with the "reference" carbonic anhydrase amino acid sequence in question (for example the sequence shown in SEQ ID No. 1) so as to achieve juxtapositioning of amino acid residues/regions which are common to both, corresponds most closely to a particular position in the reference sequence in question.

The substituted amino acid is selected such that and as previously mentioned, the modified CA retains catalytic activity (i.e. the interconversion of $CO_2$ with $HCO_3\_$ and H+) and exhibits increased stability compared to unmodified CA. The term "substituted amino acid" is intended to include natural amino acids and non-natural amino acids. Non-natural amino acids include amino acid derivatives, analogues and mimetics. As used herein, a "derivative" of an amino acid refers to a form of the amino acid in which one or more reactive groups on the compound have been derivatized with a substituent group. As used herein an "analogue" of an amino acid refers to a compound that retains chemical structures of the amino acid necessary for functional activity of the amino acid yet also contains certain chemical structures that differ from the amino acid. As used herein, a "mimetic" of an amino acid refers to a compound in that mimics the chemical conformation of the amino acid.

Preferred amino acid substitutions consist of Ala65Thr, Phe93Leu, Leu100His, Gln136Tyr, Gln136His, Lys153Leu, Leu198Met, Leu223Ser, Leu239Pro or Ala247Thr. More particularly, the modified CA of the invention comprises an amino acid sequence substantially identical to a sequence selected from the group consisting of SEQ ID NOS: 2 to 11 or functional derivatives thereof.

It will be understood that while the modified CA of the invention may comprises only one amino acid substitution at a position, or at an equivalent position, corresponding to position 65, 93, 100, 136, 153, 198, 223, 239 and 247 of SEQ ID NO 1, it may be advantagous to provide a modified CA which comprises a combination of any of the amino acid substitution mentioned above. In other words, the present invention also advantageously concernes a modified CA protein that comprises a combination of two (2×), three (3×), four (4×), five (5×), six (6×), seven (7×), eight (8×) or of nine (9×) of the amino acid substitutions mentioned above. Preferred combinations contemplated by the present invention are those shown in Table 1.

In another embodiment, the present invention concerns an isolated polynucleotide encoding a modified CA polypeptide of the invention. Preferably, the isolated polynucleotide of the invention comprises a nucleotide sequence substantially identical to a sequence selected from the group consisting of SEQ ID NOs: 12 to 21 and functional fragments thereof.

2. Vector

In another embodiment, the invention is further directed to a vector (e.g. cloning or expression vector) comprising a polynucleotide sequence of the invention.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for transcription of a nucleotide sequence in a host cell, or a "viral vector" which is designed to result in the production of a recombinant virus or virus-like particle, or "shuttle vectors", which comprise the attributes of more than one type of vector.

A number of vectors suitable for stable transfection of cells and bacteria are available to the public (e.g. plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecule of the invention.

3. Cells

In a further embodiment, the invention is also directed to a host, such as a genetically modified cell, comprising any of the polynucleotide sequence according to the invention and more preferably, a host capable of expressing the polypeptide encoded by this polynucleotide. Even more preferably, the present invention is concerned with a host cell that incorporates an expression vector or a recombinant viral vector as defined herein below.

The host cell may be any type of cell (a transiently-transfected mammalian cell line, an isolated primary cell, or insect cell, yeast (*Saccharomyces cerevisiae* or *Pichia pastoris*), plant cell, microorganism, or a bacterium (such as *E. coli*).

4. Uses of Modified CA

The modified CA proteins of the invention retain the catalytic activity of unmodified CA. Accordingly, the modified CA proteins are useful for catalysing $CO_2$. Moreover, since a modified CA protein of the invention has increased stability under high temperature compared to unmodified CA, a particular amount of this modified CA protein exhibits greater catalytic activity over time than an equal amount of unmodified CA.

The modified CA proteins of the invention can also be used in processes such as those described in the following Canadian references: 2.291.785; 2.329.113 and 2.393.016.

In addition to the foregoing uses, the modified CA proteins of the invention, because of their enhanced stability, are particularly well-suited for removing $CO_2$ from a $CO_2$ containing effluent, such as a gaseous or liquid effluent, and more particularly for transforming $CO_2$ in high temperature gaseous effluent such as industrial gaseous effluents.

EXAMPLES

The present invention will be more readily understood by referring to the following examples. These examples are illustrative of the wide range of applicability of the present invention and are not intended to limit their scope. Modifications and variations can be made therein without departing from the spirit and scope of the invention. Although any methods and materials similar or equivalent to those described herein can be used in the practice for testing of the present invention, the preferred methods and materials are described.

Example 1

Cloning of Wild-type Human Carbonic Anhydrase II (HCAII)

Human lymphocytes were isolated from 8 ml of blood, which 7 ml of PBS buffer (phosphate buffer 20 mM, pH 7.4, 150 mM NaCl) was added. This blood/PBS solution was then poured onto a 10 ml Ficoll cushion (Ficoll-Paque, Pharmacia) and centrifuged during 45 minutes at 1900 rpm/22° C. (Megafuge 1.0R, Heraeus instruments). The lymphocytes layer was washed in PBS and then centrifuged at 1900 rpm during 10 minutes to obtain a pellet. The pellet was then resuspendent in TRI-Reagent (Molecular Research inc.) was then added to the pellet for RNA isolation. mRNAs were used to form a cDNA by the SuperScriptII reverse transcriptase (Gibco/BRL) according to the manufacturer's instruction. The oligonucleotide used for the reverse transcription was 5' TTTTTTTTTTTTNV 3'.

HCAII cDNA was amplified by PCR with the following specific oligonucleotides:

```
5' ATGTCCCATCACTGGGGGTAC 3'

5' TTATTTGAAGGAAGCTTTGATTTGC 3'.
```

The amplification was carried out in a thermocycler (Applied Biosystems model 9700) according to the following program: denaturation at 94° C.×2 min followed by 30 amplification cycles: 94° C.×30 sec, 48° C.×45 sec, 72° C.×60 sec and a final extention of the products at 72° C.×7 min. The PCR product was TA-cloned in the pCR2.1 vector (Invitrogene) according to the manufacturer's instructions. The ligation products have been introduced into competent $E.\ coli$ DH5α (Gibco/BRL) and the transformants were selected on LB-ampicillin agar (100 µg/mL of ampicillin; 80 mg/L X-gal and 0.2 mM IPTG).

The HCAII sequence integrity has been confirmed by direct and reverse sequencing. The coding sequence has been cloned in the expression vector pET28a(+) (NOVAGEN) to provide the pET28a+HCAII vector. Competent $E.coli$ BL21 λDE3 pLysS have been transformed with the ligation products and the transformants were selected on LB agar with kanamycin (30 µg/mL). HCAII synthesis by transformed $E.coli$ λDE3 pLysS in LB broth has been initiated at $OD_{600}$~0.6 by adding IPTG (0.4 mM) and $ZnSO_4$ (0.5 mM). Synthesis was maintained at 37° C. during 4h00 with an agitation of 250 rpm. Recombinant carbonic anhydrase production was confirmed by SDS-PAGE.

Example 2

Preparation of Modified Carbonic Anhydrases by Random Mutagenesis by PCR

Mutagenic amplification of the HCAII coding sequence was preformed with the pET28a+HCAII vector. The following oligonucleotides were used:

```
5' CAATTCCCCTCTAGAAATAATTTTGTTTAACTTTAAGAAGGAGATAT
ACCGTGGTAATG 3'

5' GGCTTGCCTGGTGCTCGAGTCATTA 3'
```

These primers hybridize to the extremities of the HCAII coding sequence. The first primer hybridises upstream to the HCAII coding sequence to the start codon (ATG) and contains a Xbal restriction site. The second primer hydridises downstream to the HCAII coding sequence to the stop codon (TM) and contains a XhoI restriction site. The restriction sites Xbal and XhoI are useful during the cloning steps of the amplicons, as better detailed hereinafter.

The amplification reaction mixture consist of TRIS-HCl pH 8.3 at 10 mM (Sigma), KCl (Sigma) 50 mM, $MnCl_2$ (Sigma) 0.15 mM, gelatine 0.01% (Biorad), ATP 2 mM, GTP 2 mM, TTP 10 mM, CTP 10 mM (dNTP Invitrogene), primers 0.5 mM, Taq DNA polymerase 0.5 Units (Promega), plasmid 4 ng in 50 µL. The amplification was performed under the following program: first cycle: 95° C.×2 min., 55° C.×30 sec and 72° C.×30 sec and 14 cycles of 95° C.×30 sec., 55° C.×30 sec and 72° C.×30 sec.

The PCR products and the pET28a(+) vector were enzymatically cut by Xbal et XhoI restriction enzymes (Roche), and the resulting fragments were purified with the QIAquick DNA extraction gel kit (Qiagen) and ligated with T4 DNA ligase (Invitrogen). The recombinant molecules were then introduced by transformation in competent $E.coli$ BL21 λDE3 pLysS. Transformed bacteria were grown on 20 cm×20 cm petri dishes containing LB agar with kanamycin (30 µg/mL) and chloramphenicol (34 µg/mL). Bacteria were incubated at 37° C. overnight. The petri dishes harbouring approximatively 2000-3000 UFC were then photographed.

Example 3

Mutant CA Selection Harboring Increased Carbonic Anhydrase Stability

Colony Transfert

The selection method of thermostabilized carbonic anhydrase was developed according to the method developed by Krebs and Fierke. Following transformation, $E.\ coli$ colonies were transfered onto a 20 cm×20 cm nitrocellulose filter (Hybon-C Extra; Amersham). The nitrocellulose filter was then disposed with the colonies facing up, onto a second agar containing IPTG (2 mM) and $ZnSO_4$ (0.5 mM) for initiating synthesis of carbonic anhydrase recombinants. The induction was maintained during four hours at 37° C. The membrane was then placed at −80° C. for at least 30 minutes. The original agar was kept at 4° C. and the membrane was used for the enzymatic assays as described hereinafter.

Membrane Preparation for Enzymatic Assays

The membrane is defrosted at room temperature for 10 minutes. The membrane frost-defrost process induces cellular breakings during the defrosting period which support the release of the cellular contents, such as the lysosyme coded by the pLysS plasmid. This lysosyme causes the lysis of the bacteria and thus, the release of the cytoplasmic contents of the bacteria. The nitrocellulose strongly maintains the released proteins by electrostatic interactions, such as the HCAII (Human Carbonic Anhydrase II) locally over-expressed by the transferred colony. The unoccupied sites on the membrane are blocked using a 100 mM TRIS (Sigma)/10 mM NaCl (Sigma) pH 8.0/5 w.v % powder skimmed milk (Nestle) solution, during the first 10 minutes without any agitation and then 50 minutes using a 50 RPM agitation at room temperature. Then the membrane is washed five times using a 100 mM TRIS/10 mM NaCl pH 8.0 solution (1×15 minutes and 4×5 minutes). After the second 5-minute washing, the fragments of the colonies which have remained linked are removed softly using a gloved finger. After the last washing, a 25 mL pipette is rolled upon the membrane surface using an adequate pressure in order to expel a maximum quantity of buffer from the membrane. Finally, the membrane is soaked in a 25 mM TAPS (Sigma)/100 mM $Na_2SO_4$ (Fisher) pH 8.4 buffer compatible with enzymatic assays.

Example 4

CA Activity Detection

The selection method uses the hydration activity of $CO_2$ from the HCAII (Equation 1: Residual activity(%) = $\left(\frac{\text{Activity after treatment}}{\text{Activity before treatment}}\right) \times 100$.

The hydration reaction of $CO_2$ releases a proton, leading to a local acidification of the membrane, more specifically where an active HCAII is located. The membrane is coloured using the following buffer: 25 mM TAPS/100 mM $Na_2SO_4$ pH 8.4/10 mM purple m-cresol (Fisher). Then, the membrane is placed in a container designed specifically for this purpose. This container is translucent which allows for the observation of the enzymatic reaction, and contains pure $CO_2$. The $CO_2$ hydration reaction leads to a local quick color change on the membrane from purple to yellow, where the HCAII, which is able to hydrate the $CO_2$, is located. After a first control assay, the membrane is subjected to a 15 min. thermal treatment at 53° C. by soaking it in a 53° C. pre-heated buffer 25 mM TAPS/100 mM $Na_2SO_4$ pH 8.4. This is the minimal treatment necessary to completely eliminate the signal created by the native HCAII and allows the activity of the improved mutant enzymes to be highlighted. A second developing process of the membrane as described above is performed after the thermal process, and the permanent signals from stabilized HCAII are located. For every enzymatic activity assays on membranes, a numeric camera is used in order to record all the data and facilitate their later analysis.

Example 5

Identification of Thermostabilized CA Mutants

The numeric signals were analyzed using Adobe Photoshop® software to superimpose the image of the above mentioned membrane with the corresponding Petri-dish culture and identify the clones responsible for the synthesis of a stabilized mutant HACII.

The identified clones are regrown on nutrient agar in order to validate this result. The plasmidic DNA of the clones producing stabilized HCAII is purified and the DNA sequence coding these enzymes is sequenced. (See FIGS. 17 to 26)

Example 6

Purification of of Thermostabilized CA Mutants for Enzymatic Assay

The cloned recombinant CA was purified according to the following method.

The bacterial pellets were lysed with 18 mL of Lysis buffer (50 mM acetate pH 6.2 with 4 μg/mL of DNAse).

The lysed pellet solutions were centrifuged at 32 000 g during 15 minutes. The pH of the supernatant was adjusted to 6.2. The supernatants were then filtered (0.2 μm). The filtered supernatants were applied on 2 mL column of cathionic Unosphere S resin (BioRad). A first wash with 4 mL of lysis buffer followed by a second wash of 2 mL of lysis buffer with 10 mM NaCl were performed. An elution with 15 mL of lysis buffer with 75 mM NaCl was further performed.

The obtained fractions were applied onto a SDS-Page gel for the identification of fractions containing the pure CA. Then, these fractions were pooled.

The concentration of purified CA was measured at 280 nm with a molar absorption coefficient (epsilon)=$5.4 \times 10^4$ $M^{-1}$ $cm^{-1}$.

Example 7

CA Enzymatic Assay with Purified Modified CA of the Invention 0.25 mL PCR (Sarstedt) containing 250 μl of purified CA (10 μM) were incubated for 2 hours at different temperatures (55° C., 60° C., 62.5° C., 65° C. and 70° C.) in a heat bath.

The tubes were then cooled rapidly on ice for stopping the thermal denaturation. The tubes were then centrifuged (quick spin) at 13 000 RPM to obtain a pellet. The thermostability of the modified CA of the invention was determined by measuring the residual esterase activity according to the above described equation 1.

Figure 2:
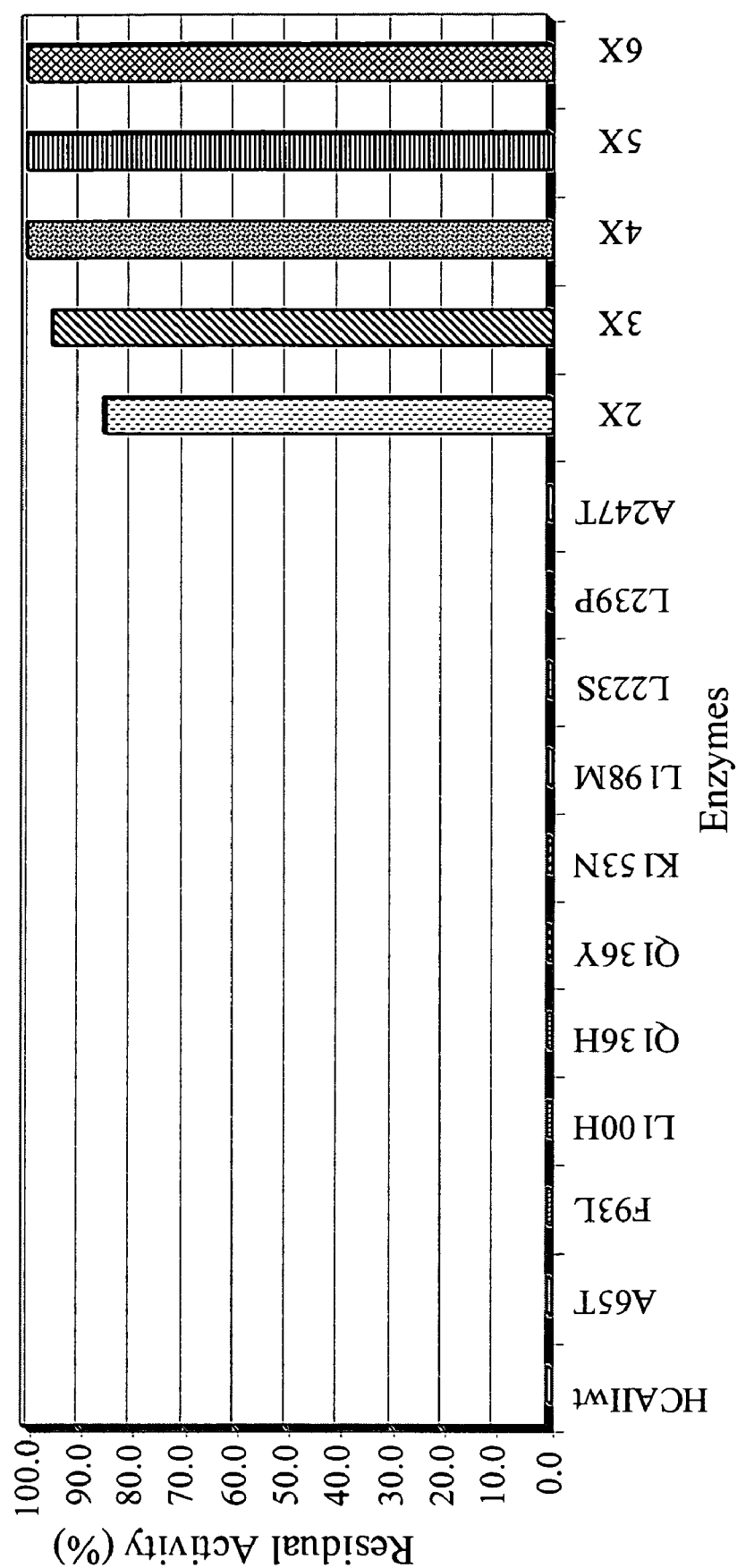
FIG. 2 shows the residual enzymatic activity of modified carbonic anhydrases II according to preferred embodiments of the invention following a 2 hour treatment at 60° C.
Figure 3:
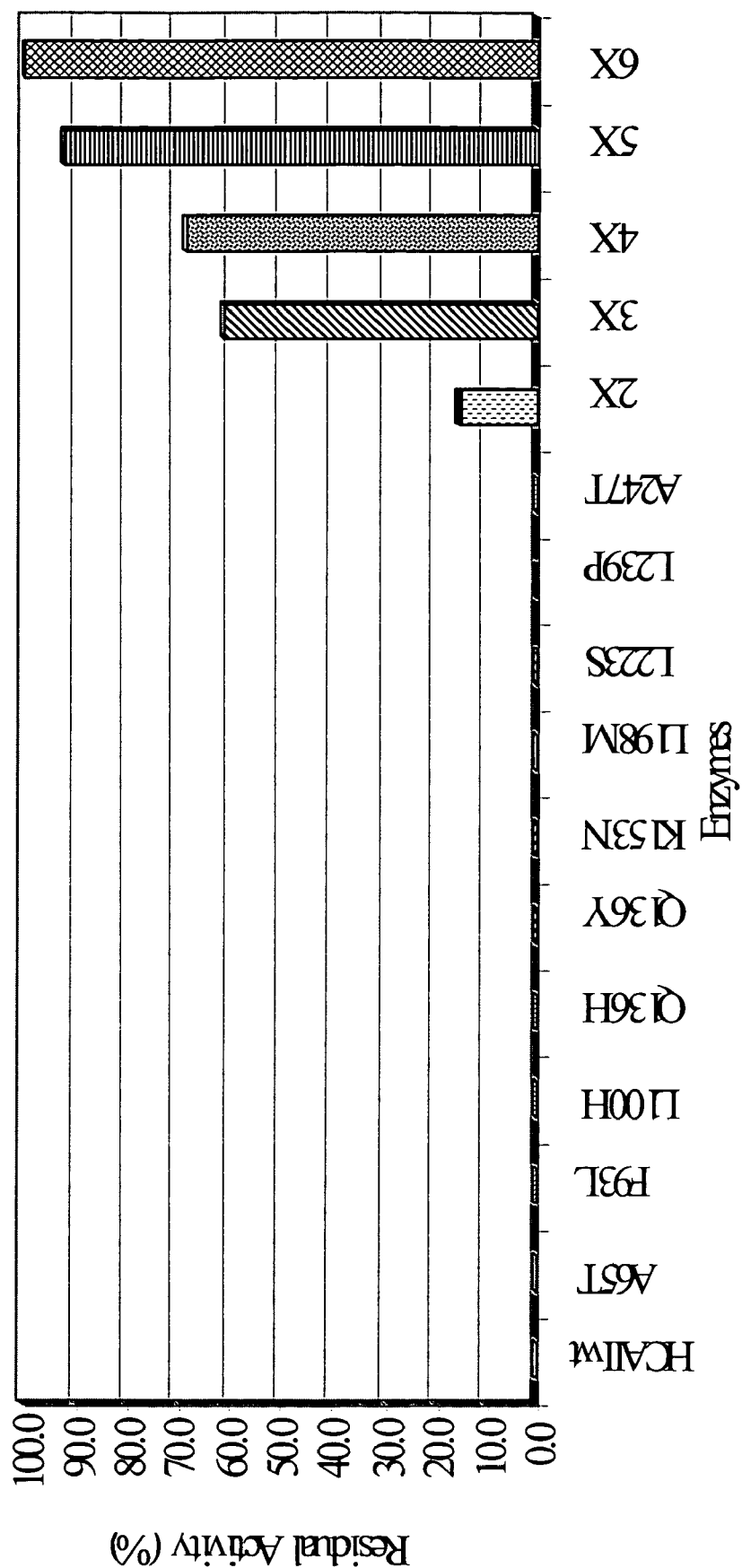
FIG. 3 shows the residual enzymatic activity of modified carbonic anhydrases II according to preferred embodiments of the invention following a 2 hour treatment at 62.5° C.
Figure 4:
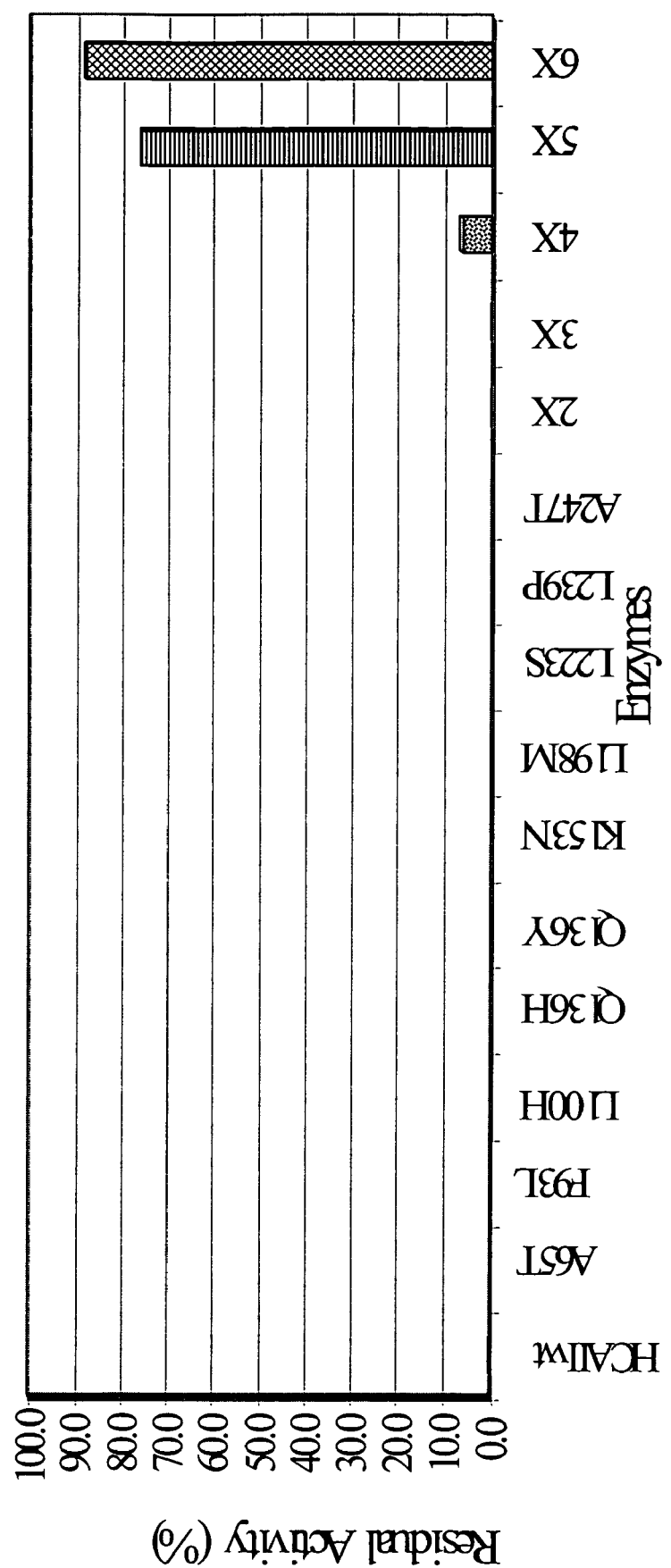
FIG. 4 shows the residual enzymatic activity of modified carbonic anhydrases II according to preferred embodiments of the invention following a 2 hour treatment at 65° C.
Figure 5:
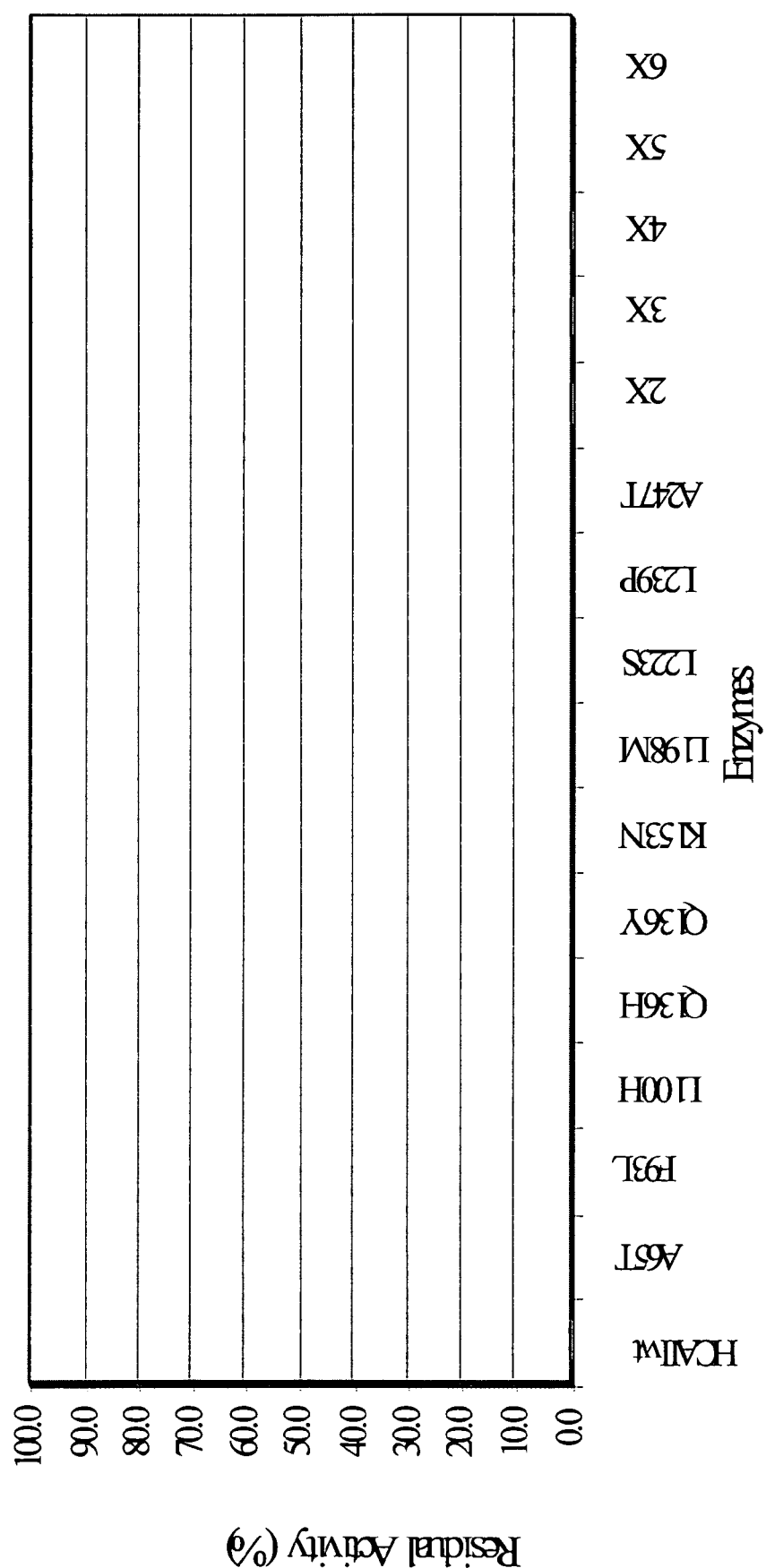
FIG. 5 shows the residual enzymatic activity of modified carbonic anhydrases II according to preferred embodiments of the invention following a 2 hour treatment at 70° C.

The esterase activity was measured in buffer TRIS (pH 8.0; 0.1 ionic force; 1% acetone; 0.5 mM pNPA at a temperature of 25° C.). The enzyme concentration used was 0.1 μM (40 uL of the treated solution). The esterase activity was measured by spectrophotometer at 348 nm. The results are shown in FIGS. 1 to 5.

REFERENCES

All publications, patents and patent applications cited herein are hereby incorporated by reference in their entirety.

1. Krebs, J., Fierke, C., 1993, J. of Biological Chemistry, Vol. 268, p. 948.
2. Jackman, J. E., Merz, K. M., Jr., & Fierke, C. A. (1996) Biochemistry 35, 16421
3. Scolnick L R, Christianson D W., 1996, Biochemistry, Vol 35, No. 51 p. 16429
4. Hunt, J A, Fierke C A., 1997, J. of Biological Chemistry, Vol. 272, No. 33, p. 20364

TABLE 1

Results of the residual enzymatic activity of modified carbonic anhydrase following a 2 hour treatment under high temperature conditions.

| ID. | Mutations | 55 C. | 60 C. | 62.5 | 65 C. | 70 C. |
|---|---|---|---|---|---|---|
| 0 | HCAIIwt | 12.6% | 0.0% | 0.0% | 0.0% | 0.0% |
| 1 | A65T | 67.9% | 0.0% | 0.0% | 0.0% | 0.0% |
| 2 | F93L | 62.7% | 0.0% | 0.0% | 0.0% | 0.0% |
| 3 | L100H | 60.7% | 0.0% | 0.0% | 0.0% | 0.0% |
| 4 | Q136H | 51.5% | 0.0% | 0.0% | 0.0% | 0.0% |
| 5 | Q136Y | 62.7% | 0.0% | 0.0% | 0.0% | 0.0% |
| 6 | K153L | 55.0% | 0.0% | 0.0% | 0.0% | 0.0% |
| 7 | L198M | 59.7% | 0.0% | 0.0% | 0.0% | 0.0% |
| 8 | L223S | 83.0% | 0.0% | 0.0% | 0.0% | 0.0% |

TABLE 1-continued

Results of the residual enzymatic activity of modified carbonic anhydrase following a 2 hour treatment under high temperature conditions.

| ID. | Mutations | 55 C. | 60 C. | 62.5 | 65 C. | 70 C. |
|---|---|---|---|---|---|---|
| 9 | L239P | 70.8% | 0.0% | 0.0% | 0.0% | 0.0% |
| 10 | A247T | 84.4% | 0.0% | 0.0% | 0.0% | 0.0% |
| 1 + 3 | 2X | 100.0% | 85.0% | 15.3% | 0.0% | 0.0% |
| 1 + 3 + 9 | 3X | 100.0% | 95.0% | 61.0% | 0.0% | 0.0% |
| 1 + 3 + 6 + 9 | 4X | 100.0% | 100.0% | 68.2% | 6.6% | 0.0% |
| 1 + 3 + 6 + 8 + 9 | 5X | 100.0% | 100.0% | 92.4% | 76.4% | 0.0% |
| 1 + 3 + 6 + 8 + 9 + 10 | 6X | 100.0% | 100.0% | 100.0% | 88.4% | 0.0% |

The invention claimed is:

1. A modified carbonic anhydrase polypeptide having increased thermal stability compared to unmodified native carbonic anhydrase, said modified carbonic anhydrase comprising the amino acid sequence of SEQ ID NO: 1, with at least two amino acid substitutions selected from the group consisting of Leu100His, Gln136Tyr, Lys153Leu, and Ala247Thr.

2. The modified carbonic anhydrase of claim 1, consisting of the amino acid sequence of SEQ ID NO: 11.

3. The modified carbonic anhydrase of claim 1, being encoded by the nucleic acid sequence of SEQ ID NO: 21.

* * * * *

SEQUENCE LISTING

```
<160> NUMBER OF SEQ ID NOS: 21

<210> SEQ ID NO 1
<211> LENGTH: 260
<212> TYPE: PRT
<213> ORGANISM: Homo sapien

<400> SEQUENCE: 1

Met Ser His His Trp Gly Tyr Gly Lys His Asn Gly Pro Glu His
                  5                   10                  15

Trp His Lys Asp Phe Pro Ile Ala Lys Gly Glu Arg Gln Ser Pro
                 20                   25                  30

Val Asp Ile Asp Thr His Thr Ala Lys Tyr Asp Pro Ser Leu Lys
                 35                   40                  45

Pro Leu Ser Val Ser Tyr Asp Gln Ala Thr Ser Leu Arg Ile Leu
                 50                   55                  60

Asn Asn Gly His Ala Phe Asn Val Glu Phe Asp Asp Ser Gln Asp
                 65                   70                  75

Lys Ala Val Leu Lys Gly Gly Pro Leu Asp Gly Thr Tyr Arg Leu
                 80                   85                  90

Ile Gln Phe His Phe His Trp Gly Ser Leu Asp Gly Gln Gly Ser
                 95                  100                 105

Glu His Thr Val Asp Lys Lys Lys Tyr Ala Ala Glu Leu His Leu
                110                  115                 120

Val His Trp Asn Thr Lys Tyr Gly Asp Phe Gly Lys Ala Val Gln
                125                  130                 135

Gln Pro Asp Gly Leu Ala Val Leu Gly Ile Phe Leu Lys Val Gly
                140                  145                 150

Ser Ala Lys Pro Gly Leu Gln Lys Val Val Asp Val Leu Asp Ser
                155                  160                 165

Ile Lys Thr Lys Gly Lys Ser Ala Asp Phe Thr Asn Phe Asp Pro
                170                  175                 180

Arg Gly Leu Leu Pro Glu Ser Leu Asp Tyr Trp Thr Tyr Pro Gly
                185                  190                 195

Ser Leu Thr Thr Pro Pro Leu Leu Glu Cys Val Thr Trp Ile Val
                200                  205                 210

Leu Lys Glu Pro Ile Ser Val Ser Ser Glu Gln Val Leu Lys Phe
                215                  220                 225

Arg Lys Leu Asn Phe Asn Gly Glu Gly Glu Pro Glu Glu Leu Met
                230                  235                 240

Val Asp Asn Trp Arg Pro Ala Gln Pro Leu Lys Asn Arg Gln Ile
```

-continued

```
                      245                 250                 255
Lys Ala Ser Phe Lys
                260

<210> SEQ ID NO 2
<211> LENGTH: 260
<212> TYPE: PRT
<213> ORGANISM: Homo sapien

<400> SEQUENCE: 2

Met Ser His His Trp Gly Tyr Gly Lys His Asn Gly Pro Glu His
                  5                  10                  15

Trp His Lys Asp Phe Pro Ile Ala Lys Gly Glu Arg Gln Ser Pro
                 20                  25                  30

Val Asp Ile Asp Thr His Thr Ala Lys Tyr Asp Pro Ser Leu Lys
                 35                  40                  45

Pro Leu Ser Val Ser Tyr Asp Gln Ala Thr Ser Leu Arg Ile Leu
                 50                  55                  60

Asn Asn Gly His Thr Phe Asn Val Glu Phe Asp Asp Ser Gln Asp
                 65                  70                  75

Lys Ala Val Leu Lys Gly Gly Pro Leu Asp Gly Thr Tyr Arg Leu
                 80                  85                  90

Ile Gln Phe His Phe His Trp Gly Ser Leu Asp Gly Gln Gly Ser
                 95                 100                 105

Glu His Thr Val Asp Lys Lys Lys Tyr Ala Ala Glu Leu His Leu
                110                 115                 120

Val His Trp Asn Thr Lys Tyr Gly Asp Phe Gly Lys Ala Val Gln
                125                 130                 135

Gln Pro Asp Gly Leu Ala Val Leu Gly Ile Phe Leu Lys Val Gly
                140                 145                 150

Ser Ala Lys Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260

<210> SEQ ID NO 3
<211> LENGTH: 260
<212> TYPE: PRT
<213> ORGANISM: Homo sapien

<400> SEQUENCE: 3

Met Ser His His Trp Gly Tyr Gly Lys His Asn Gly Pro Glu His
                  5                  10                  15

Trp His Lys Asp Phe Pro Ile Ala Lys Gly Glu Arg Gln Ser Pro
```

```
                20                  25                  30
Val Asp Ile Asp Thr His Thr Ala Lys Tyr Asp Pro Ser Leu Lys
                35                  40                  45

Pro Leu Ser Val Ser Tyr Asp Gln Ala Thr Ser Leu Arg Ile Leu
                50                  55                  60

Asn Asn Gly His Ala Phe Asn Val Glu Phe Asp Asp Ser Gln Asp
                65                  70                  75

Lys Ala Val Leu Lys Gly Gly Pro Leu Asp Gly Thr Tyr Arg Leu
                80                  85                  90

Ile Gln Leu His Phe His Trp Gly Ser Leu Asp Gly Gln Gly Ser
                95                 100                 105

Glu His Thr Val Asp Lys Lys Lys Tyr Ala Ala Glu Leu His Leu
               110                 115                 120

Val His Trp Asn Thr Lys Tyr Gly Asp Phe Gly Lys Ala Val Gln
               125                 130                 135

Gln Pro Asp Gly Leu Ala Val Leu Gly Ile Phe Leu Lys Val Gly
               140                 145                 150

Ser Ala Lys Pro Gly Leu Gln Lys Val Val Asp Val Leu Asp Ser
               155                 160                 165

Ile Lys Thr Lys Gly Lys Ser Ala Asp Phe Thr Asn Phe Asp Pro
               170                 175                 180

Arg Gly Leu Leu Pro Glu Ser Leu Asp Tyr Trp Thr Tyr Pro Gly
               185                 190                 195

Ser Leu Thr Thr Pro Pro Leu Leu Glu Cys Val Thr Trp Ile Val
               200                 205                 210

Leu Lys Glu Pro Ile Ser Val Ser Ser Glu Gln Val Leu Lys Phe
               215                 220                 225

Arg Lys Leu Asn Phe Asn Gly Glu Gly Glu Pro Glu Glu Leu Met
               230                 235                 240

Val Asp Asn Trp Arg Pro Ala Gln Pro Leu Lys Asn Arg Gln Ile
               245                 250                 255

Lys Ala Ser Phe Lys
               260

<210> SEQ ID NO 4
<211> LENGTH: 260
<212> TYPE: PRT
<213> ORGANISM: Homo sapien

<400> SEQUENCE: 4

Met Ser His His Trp Gly Tyr Gly Lys His Asn Gly Pro Glu His
                 5                  10                  15

Trp His Lys Asp Phe Pro Ile Ala Lys Gly Glu Arg Gln Ser Pro
                20                  25                  30

Val Asp Ile Asp Thr His Thr Ala Lys Tyr Asp Pro Ser Leu Lys
                35                  40                  45

Pro Leu Ser Val Ser Tyr Asp Gln Ala Thr Ser Leu Arg Ile Leu
                50                  55                  60

Asn Asn Gly His Ala Phe Asn Val Glu Phe Asp Asp Ser Gln Asp
                65                  70                  75

Lys Ala Val Leu Lys Gly Gly Pro Leu Asp Gly Thr Tyr Arg Leu
                80                  85                  90

Ile Gln Phe His Phe His Trp Gly Ser His Asp Gly Gln Gly Ser
                95                 100                 105
```

```
Glu His Thr Val Asp Lys Lys Tyr Ala Ala Glu Leu His Leu
            110                 115                 120

Val His Trp Asn Thr Lys Tyr Gly Asp Phe Gly Lys Ala Val Gln
            125                 130                 135

Gln Pro Asp Gly Leu Ala Val Leu Gly Ile Phe Leu Lys Val Gly
            140                 145                 150

Ser Ala Lys Pro Gly Leu Gln Lys Val Val Asp Val Leu Asp Ser
            155                 160                 165

Ile Lys Thr Lys Gly Lys Ser Ala Asp Phe Thr Asn Phe Asp Pro
            170                 175                 180

Arg Gly Leu Leu Pro Glu Ser Leu Asp Tyr Trp Thr Tyr Pro Gly
            185                 190                 195

Ser Leu Thr Thr Pro Pro Leu Leu Glu Cys Val Thr Trp Ile Val
            200                 205                 210

Leu Lys Glu Pro Ile Ser Val Ser Ser Glu Gln Val Leu Lys Phe
            215                 220                 225

Arg Lys Leu Asn Phe Asn Gly Glu Gly Glu Pro Glu Glu Leu Met
            230                 235                 240

Val Asp Asn Trp Arg Pro Ala Gln Pro Leu Lys Asn Arg Gln Ile
            245                 250                 255

Lys Ala Ser Phe Lys
            260

<210> SEQ ID NO 5
<211> LENGTH: 260
<212> TYPE: PRT
<213> ORGANISM: Homo sapien

<400> SEQUENCE: 5

Met Ser His His Trp Gly Tyr Gly Lys His Asn Gly Pro Glu His
              5                  10                  15

Trp His Lys Asp Phe Pro Ile Ala Lys Gly Glu Arg Gln Ser Pro
             20                  25                  30

Val Asp Ile Asp Thr His Thr Ala Lys Tyr Asp Pro Ser Leu Lys
             35                  40                  45

Pro Leu Ser Val Ser Tyr Asp Gln Ala Thr Ser Leu Arg Ile Leu
             50                  55                  60

Asn Asn Gly His Ala Phe Asn Val Glu Phe Asp Asp Ser Gln Asp
             65                  70                  75

Lys Ala Val Leu Lys Gly Gly Pro Leu Asp Gly Thr Tyr Arg Leu
             80                  85                  90

Ile Gln Phe His Phe His Trp Gly Ser Leu Asp Gly Gln Gly Ser
             95                 100                 105

Glu His Thr Val Asp Lys Lys Tyr Ala Ala Glu Leu His Leu
            110                 115                 120

Val His Trp Asn Thr Lys Tyr Gly Asp Phe Gly Lys Ala Val Gln
            125                 130                 135

Tyr Pro Asp Gly Leu Ala Val Leu Gly Ile Phe Leu Lys Val Gly
            140                 145                 150

Ser Ala Lys Pro Gly Leu Gln Lys Val Val Asp Val Leu Asp Ser
            155                 160                 165

Ile Lys Thr Lys Gly Lys Ser Ala Asp Phe Thr Asn Phe Asp Pro
            170                 175                 180

Arg Gly Leu Leu Pro Glu Ser Leu Asp Tyr Trp Thr Tyr Pro Gly
            185                 190                 195
```

```
Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260

<210> SEQ ID NO 6
<211> LENGTH: 260
<212> TYPE: PRT
<213> ORGANISM: Homo sapien

<400> SEQUENCE: 6

Met Ser His His Trp Gly Tyr Gly Lys His Asn Gly Pro Glu His
                5                   10                  15

Trp His Lys Asp Phe Pro Ile Ala Lys Gly Glu Arg Gln Ser Pro
                20                  25                  30

Val Asp Ile Asp Thr His Thr Ala Lys Tyr Asp Pro Ser Leu Lys
                35                  40                  45

Pro Leu Ser Val Ser Tyr Asp Gln Ala Thr Ser Leu Arg Ile Leu
                50                  55                  60

Asn Asn Gly His Ala Phe Asn Val Glu Phe Asp Asp Ser Gln Asp
                65                  70                  75

Lys Ala Val Leu Lys Gly Gly Pro Leu Asp Gly Thr Tyr Arg Leu
                80                  85                  90

Ile Gln Phe His Phe His Trp Gly Ser Leu Asp Gly Gln Gly Ser
                95                  100                 105

Glu His Thr Val Asp Lys Lys Lys Tyr Ala Ala Glu Leu His Leu
                110                 115                 120

Val His Trp Asn Thr Lys Tyr Gly Asp Phe Gly Lys Ala Val Gln
                125                 130                 135

His Pro Asp Gly Leu Ala Val Leu Gly Ile Phe Leu Lys Val Gly
                140                 145                 150

Ser Ala Lys Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260
```

<210> SEQ ID NO 7
<211> LENGTH: 260
<212> TYPE: PRT
<213> ORGANISM: Homo sapien

<400> SEQUENCE: 7

Met Ser His His Trp Gly Tyr Gly Lys His Asn Gly Pro Glu His
                  5                  10                  15

Trp His Lys Asp Phe Pro Ile Ala Lys Gly Glu Arg Gln Ser Pro
                 20                  25                  30

Val Asp Ile Asp Thr His Thr Ala Lys Tyr Asp Pro Ser Leu Lys
                 35                  40                  45

Pro Leu Ser Val Ser Tyr Asp Gln Ala Thr Ser Leu Arg Ile Leu
                 50                  55                  60

Asn Asn Gly His Ala Phe Asn Val Glu Phe Asp Ser Gln Asp
                 65                  70                  75

Lys Ala Val Leu Lys Gly Gly Pro Leu Asp Gly Thr Tyr Arg Leu
                 80                  85                  90

Ile Gln Phe His Phe His Trp Gly Ser Leu Asp Gly Gln Gly Ser
                 95                 100                 105

Glu His Thr Val Asp Lys Lys Lys Tyr Ala Ala Glu Leu His Leu
                110                 115                 120

Val His Trp Asn Thr Lys Tyr Gly Asp Phe Gly Lys Ala Val Gln
                125                 130                 135

Gln Pro Asp Gly Leu Ala Val Leu Gly Ile Phe Leu Lys Val Gly
                140                 145                 150

Ser Ala Leu Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Ala Gln Pro Leu Lys Asn Arg Gln Ile
                245                 250                 255

Lys Ala Ser Phe Lys
                260

<210> SEQ ID NO 8
<211> LENGTH: 260
<212> TYPE: PRT
<213> ORGANISM: Homo sapien

<400> SEQUENCE: 8

Met Ser His His Trp Gly Tyr Gly Lys His Asn Gly Pro Glu His
                  5                  10                  15

Trp His Lys Asp Phe Pro Ile Ala Lys Gly Glu Arg Gln Ser Pro
                 20                  25                  30

Val Asp Ile Asp Thr His Thr Ala Lys Tyr Asp Pro Ser Leu Lys
                 35                  40                  45

Pro Leu Ser Val Ser Tyr Asp Gln Ala Thr Ser Leu Arg Ile Leu

```
                     50                  55                  60
Asn Asn Gly His Ala Phe Asn Val Glu Phe Asp Asp Ser Gln Asp
                 65                  70                  75
Lys Ala Val Leu Lys Gly Gly Pro Leu Asp Gly Thr Tyr Arg Leu
             80                  85                  90
Ile Gln Phe His Phe His Trp Gly Ser Leu Asp Gly Gln Gly Ser
         95                  100                 105
Glu His Thr Val Asp Lys Lys Tyr Ala Ala Glu Leu His Leu
            110                 115                 120
Val His Trp Asn Thr Lys Tyr Gly Asp Phe Gly Lys Ala Val Gln
                125                 130                 135
Gln Pro Asp Gly Leu Ala Val Leu Gly Ile Phe Leu Lys Val Gly
                140                 145                 150
Ser Ala Lys Pro Gly Leu Gln Lys Val Val Asp Val Leu Asp Ser
                155                 160                 165
Ile Lys Thr Lys Gly Lys Ser Ala Asp Phe Thr Asn Phe Asp Pro
                170                 175                 180
Arg Gly Leu Leu Pro Glu Ser Leu Asp Tyr Trp Thr Tyr Pro Gly
                185                 190                 195
Ser Met Thr Thr Pro Pro Leu Leu Glu Cys Val Thr Trp Ile Val
                200                 205                 210
Leu Lys Glu Pro Ile Ser Val Ser Ser Glu Gln Val Leu Lys Phe
                215                 220                 225
Arg Lys Leu Asn Phe Asn Gly Glu Gly Glu Pro Glu Glu Leu Met
                230                 235                 240
Val Asp Asn Trp Arg Pro Ala Gln Pro Leu Lys Asn Arg Gln Ile
                245                 250                 255
Lys Ala Ser Phe Lys
                260

<210> SEQ ID NO 9
<211> LENGTH: 260
<212> TYPE: PRT
<213> ORGANISM: Homo sapien

<400> SEQUENCE: 9

Met Ser His His Trp Gly Tyr Gly Lys His Asn Gly Pro Glu His
                 5                  10                  15
Trp His Lys Asp Phe Pro Ile Ala Lys Gly Glu Arg Gln Ser Pro
                20                  25                  30
Val Asp Ile Asp Thr His Thr Ala Lys Tyr Asp Pro Ser Leu Lys
                35                  40                  45
Pro Leu Ser Val Ser Tyr Asp Gln Ala Thr Ser Leu Arg Ile Leu
                50                  55                  60
Asn Asn Gly His Ala Phe Asn Val Glu Phe Asp Asp Ser Gln Asp
                65                  70                  75
Lys Ala Val Leu Lys Gly Gly Pro Leu Asp Gly Thr Tyr Arg Leu
                80                  85                  90
Ile Gln Phe His Phe His Trp Gly Ser Leu Asp Gly Gln Gly Ser
                95                  100                 105
Glu His Thr Val Asp Lys Lys Lys Tyr Ala Ala Glu Leu His Leu
                110                 115                 120
Val His Trp Asn Thr Lys Tyr Gly Asp Phe Gly Lys Ala Val Gln
                125                 130                 135
```

```
Gln Pro Asp Gly Leu Ala Val Leu Gly Ile Phe Leu Lys Val Gly
            140                 145                 150

Ser Ala Lys Pro Gly Leu Gln Lys Val Val Asp Val Leu Asp Ser
            155                 160                 165

Ile Lys Thr Lys Gly Lys Ser Ala Asp Phe Thr Asn Phe Asp Pro
            170                 175                 180

Arg Gly Leu Leu Pro Glu Ser Leu Asp Tyr Trp Thr Tyr Pro Gly
            185                 190                 195

Ser Leu Thr Thr Pro Pro Leu Leu Glu Cys Val Thr Trp Ile Val
            200                 205                 210

Leu Lys Glu Pro Ile Ser Val Ser Ser Glu Gln Val Ser Lys Phe
            215                 220                 225

Arg Lys Leu Asn Phe Asn Gly Glu Gly Glu Pro Glu Glu Leu Met
            230                 235                 240

Val Asp Asn Trp Arg Pro Ala Gln Pro Leu Lys Asn Arg Gln Ile
            245                 250                 255

Lys Ala Ser Phe Lys
            260

<210> SEQ ID NO 10
<211> LENGTH: 260
<212> TYPE: PRT
<213> ORGANISM: Homo sapien

<400> SEQUENCE: 10

Met Ser His His Trp Gly Tyr Gly Lys His Asn Gly Pro Glu His
              5                  10                  15

Trp His Lys Asp Phe Pro Ile Ala Lys Gly Glu Arg Gln Ser Pro
             20                  25                  30

Val Asp Ile Asp Thr His Thr Ala Lys Tyr Asp Pro Ser Leu Lys
             35                  40                  45

Pro Leu Ser Val Ser Tyr Asp Gln Ala Thr Ser Leu Arg Ile Leu
             50                  55                  60

Asn Asn Gly His Ala Phe Asn Val Glu Phe Asp Asp Ser Gln Asp
             65                  70                  75

Lys Ala Val Leu Lys Gly Gly Pro Leu Asp Gly Thr Tyr Arg Leu
             80                  85                  90

Ile Gln Phe His Phe His Trp Gly Ser Leu Asp Gly Gln Gly Ser
             95                 100                 105

Glu His Thr Val Asp Lys Lys Lys Tyr Ala Ala Glu Leu His Leu
            110                 115                 120

Val His Trp Asn Thr Lys Tyr Gly Asp Phe Gly Lys Ala Val Gln
            125                 130                 135

Gln Pro Asp Gly Leu Ala Val Leu Gly Ile Phe Leu Lys Val Gly
            140                 145                 150

Ser Ala Lys Pro Gly Leu Gln Lys Val Val Asp Val Leu Asp Ser
            155                 160                 165

Ile Lys Thr Lys Gly Lys Ser Ala Asp Phe Thr Asn Phe Asp Pro
            170                 175                 180

Arg Gly Leu Leu Pro Glu Ser Leu Asp Tyr Trp Thr Tyr Pro Gly
            185                 190                 195

Ser Leu Thr Thr Pro Pro Leu Leu Glu Cys Val Thr Trp Ile Val
            200                 205                 210

Leu Lys Glu Pro Ile Ser Val Ser Ser Glu Gln Val Leu Lys Phe
            215                 220                 225
```

```
Arg Lys Leu Asn Phe Asn Gly Glu Gly Glu Pro Glu Glu Pro Met
                230                 235                 240

Val Asp Asn Trp Arg Pro Ala Gln Pro Leu Lys Asn Arg Gln Ile
                245                 250                 255

Lys Ala Ser Phe Lys
                260

<210> SEQ ID NO 11
<211> LENGTH: 260
<212> TYPE: PRT
<213> ORGANISM: Homo sapien

<400> SEQUENCE: 11

Met Ser His His Trp Gly Tyr Gly Lys His Asn Gly Pro Glu His
                  5                  10                  15

Trp His Lys Asp Phe Pro Ile Ala Lys Gly Glu Arg Gln Ser Pro
                 20                  25                  30

Val Asp Ile Asp Thr His Thr Ala Lys Tyr Asp Pro Ser Leu Lys
                 35                  40                  45

Pro Leu Ser Val Ser Tyr Asp Gln Ala Thr Ser Leu Arg Ile Leu
                 50                  55                  60

Asn Asn Gly His Ala Phe Asn Val Glu Phe Asp Asp Ser Gln Asp
                 65                  70                  75

Lys Ala Val Leu Lys Gly Gly Pro Leu Asp Gly Thr Tyr Arg Leu
                 80                  85                  90

Ile Gln Phe His Phe His Trp Gly Ser Leu Asp Gly Gln Gly Ser
                 95                 100                 105

Glu His Thr Val Asp Lys Lys Lys Tyr Ala Ala Glu Leu His Leu
                110                 115                 120

Val His Trp Asn Thr Lys Tyr Gly Asp Phe Gly Lys Ala Val Gln
                125                 130                 135

Gln Pro Asp Gly Leu Ala Val Leu Gly Ile Phe Leu Lys Val Gly
                140                 145                 150

Ser Ala Lys Pro Gly Leu Gln Lys Val Val Asp Val Leu Asp Ser
                155                 160                 165

Ile Lys Thr Lys Gly Lys Ser Ala Asp Phe Thr Asn Phe Asp Pro
                170                 175                 180

Arg Gly Leu Leu Pro Glu Ser Leu Asp Tyr Trp Thr Tyr Pro Gly
                185                 190                 195

Ser Leu Thr Thr Pro Pro Leu Leu Glu Cys Val Thr Trp Ile Val
                200                 205                 210

Leu Lys Glu Pro Ile Ser Val Ser Ser Glu Gln Val Leu Lys Phe
                215                 220                 225

Arg Lys Leu Asn Phe Asn Gly Glu Gly Glu Pro Glu Glu Leu Met
                230                 235                 240

Val Asp Asn Trp Arg Pro Thr Gln Pro Leu Lys Asn Arg Gln Ile
                245                 250                 255

Lys Ala Ser Phe Lys
                260

<210> SEQ ID NO 12
<211> LENGTH: 783
<212> TYPE: DNA
<213> ORGANISM: Homo sapiens

<400> SEQUENCE: 12
```

```
atgtcccatc actgggggta cggcaaacac aacggacctg agcactggca taaggacttc      60
cccattgcca agggagagcg ccagtcccct gttgacatcg acactcatac agccaagtat     120
gacccttccc tgaagcccct gtctgtttcc tatgatcaag caacttccct gaggatcctc     180
aacaatggtc atactttcaa cgtggagttt gatgactctc aggacaaagc agtgctcaag     240
ggaggacccc tggatggcac ttacagattg attcagtttc actttcactg gggttcactt     300
gatggacaag gttcagagca tactgtggat aaaagaaat atgctgcaga acttcacttg      360
gttcactgga acaccaaata tggggatttt gggaaagctg tgcagcaacc tgatggactg     420
gccgttctag gtattttttt gaaggttggc agcgctaaac cgggccttca gaaagttgtt     480
gatgtgctgg attccattaa aacaaagggc aagagtgctg acttcactaa cttcgatcct     540
cgtggcctcc ttcctgaatc cctggattac tggacctacc caggctcact gaccacccct     600
cctcttctgg aatgtgtgac ctggattgtg ctcaaggaac ccatcagcgt cagcagcgag     660
caggtgttga aattccgtaa acttaacttc aatggggagg gtgaacccga agaactgatg     720
gtggacaact ggcgcccagc tcagccactg aagaacaggc aaatcaaagc ttccttcaaa     780
taa                                                                    783

<210> SEQ ID NO 13
<211> LENGTH: 783
<212> TYPE: DNA
<213> ORGANISM: Homo sapiens

<400> SEQUENCE: 13
atgtcccatc actgggggta cggcaaacac aacggacctg agcactggca taaggacttc      60
cccattgcca agggagagcg ccagtcccct gttgacatcg acactcatac agccaagtat     120
gacccttccc tgaagcccct gtctgtttcc tatgatcaag caacttccct gaggatcctc     180
aacaatggtc atgctttcaa cgtggagttt gatgactctc aggacaaagc agtgctcaag     240
ggaggacccc tggatggcac ttacagattg attcagttgc actttcactg gggttcactt     300
gatggacaag gttcagagca tactgtggat aaaagaaat atgctgcaga acttcacttg      360
gttcactgga acaccaaata tggggatttt gggaaagctg tgcagcaacc tgatggactg     420
gccgttctag gtattttttt gaaggttggc agcgctaaac cgggccttca gaaagttgtt     480
gatgtgctgg attccattaa aacaaagggc aagagtgctg acttcactaa cttcgatcct     540
cgtggcctcc ttcctgaatc cctggattac tggacctacc caggctcact gaccacccct     600
cctcttctgg aatgtgtgac ctggattgtg ctcaaggaac ccatcagcgt cagcagcgag     660
caggtgttga aattccgtaa acttaacttc aatggggagg gtgaacccga agaactgatg     720
gtggacaact ggcgcccagc tcagccactg aagaacaggc aaatcaaagc ttccttcaaa     780
taa                                                                    783

<210> SEQ ID NO 14
<211> LENGTH: 783
<212> TYPE: DNA
<213> ORGANISM: Homo sapiens

<400> SEQUENCE: 14
atgtcccatc actgggggta cggcaaacac aacggacctg agcactggca taaggacttc      60
cccattgcca agggagagcg ccagtcccct gttgacatcg acactcatac agccaagtat     120
gacccttccc tgaagcccct gtctgtttcc tatgatcaag caacttccct gaggatcctc     180
```

| | |
|---|---|
| aacaatggtc atgctttcaa cgtggagttt gatgactctc aggacaaagc agtgctcaag | 240 |
| ggaggacccc tggatggcac ttacagattg attcagtttc actttcactg gggttcacat | 300 |
| gatggacaag gttcagagca tactgtggat aaaaagaaat atgctgcaga acttcacttg | 360 |
| gttcactgga acaccaaata tggggatttt gggaaagctg tgcagcaacc tgatggactg | 420 |
| gccgttctag gtattttttt gaaggttggc agcgctaaac cgggccttca gaaagttgtt | 480 |
| gatgtgctgg attccattaa acaaagggc aagagtgctg acttcactaa cttcgatcct | 540 |
| cgtggcctcc ttcctgaatc cctggattac tggacctacc caggctcact gaccaccct | 600 |
| cctcttctgg aatgtgtgac ctggattgtg ctcaaggaac ccatcagcgt cagcagcgag | 660 |
| caggtgttga aattccgtaa acttaacttc aatggggagg gtgaacccga agaactgatg | 720 |
| gtggacaact ggcgcccagc tcagccactg aagaacaggc aaatcaaagc ttccttcaaa | 780 |
| taa | 783 |

<210> SEQ ID NO 15
<211> LENGTH: 783
<212> TYPE: DNA
<213> ORGANISM: Homo sapiens

<400> SEQUENCE: 15

| | |
|---|---|
| atgtcccatc actgggggta cggcaaacac aacggacctg agcactggca taaggacttc | 60 |
| cccattgcca agggagagcg ccagtcccct gttgacatcg acactcatac agccaagtat | 120 |
| gacccttccc tgaagcccct gtctgttttcc tatgatcaag caacttccct gaggatcctc | 180 |
| aacaatggtc atgctttcaa cgtggagttt gatgactctc aggacaaagc agtgctcaag | 240 |
| ggaggacccc tggatggcac ttacagattg attcagtttc actttcactg gggttcactt | 300 |
| gatggacaag gttcagagca tactgtggat aaaaagaaat atgctgcaga acttcacttg | 360 |
| gttcactgga acaccaaata tggggatttt gggaaagctg tgcagtatcc tgatggactg | 420 |
| gccgttctag gtattttttt gaaggttggc agcgctaaac cgggccttca gaaagttgtt | 480 |
| gatgtgctgg attccattaa acaaagggc aagagtgctg acttcactaa cttcgatcct | 540 |
| cgtggcctcc ttcctgaatc cctggattac tggacctacc caggctcact gaccaccct | 600 |
| cctcttctgg aatgtgtgac ctggattgtg ctcaaggaac ccatcagcgt cagcagcgag | 660 |
| caggtgttga aattccgtaa acttaacttc aatggggagg gtgaacccga agaactgatg | 720 |
| gtggacaact ggcgcccagc tcagccactg aagaacaggc aaatcaaagc ttccttcaaa | 780 |
| taa | 783 |

<210> SEQ ID NO 16
<211> LENGTH: 783
<212> TYPE: DNA
<213> ORGANISM: Homo sapiens

<400> SEQUENCE: 16

| | |
|---|---|
| atgtcccatc actgggggta cggcaaacac aacggacctg agcactggca taaggacttc | 60 |
| cccattgcca agggagagcg ccagtcccct gttgacatcg acactcatac agccaagtat | 120 |
| gacccttccc tgaagcccct gtctgttttcc tatgatcaag caacttccct gaggatcctc | 180 |
| aacaatggtc atgctttcaa cgtggagttt gatgactctc aggacaaagc agtgctcaag | 240 |
| ggaggacccc tggatggcac ttacagattg attcagtttc actttcactg gggttcactt | 300 |
| gatggacaag gttcagagca tactgtggat aaaaagaaat atgctgcaga acttcacttg | 360 |
| gttcactgga acaccaaata tggggatttt gggaaagctg tgcagcatcc tgatggactg | 420 |

```
gccgttctag gtatttttt gaaggttggc agcgctaaac cgggccttca gaaagttgtt    480
gatgtgctgg attccattaa acaaagggc aagagtgctg acttcactaa cttcgatcct    540
cgtggcctcc ttcctgaatc cctggattac tggacctacc caggctcact gaccacccct    600
cctcttctgg aatgtgtgac ctggattgtg ctcaaggaac ccatcagcgt cagcagcgag    660
caggtgttga aattccgtaa acttaacttc aatgggagg gtgaacccga agaactgatg    720
gtggacaact ggcgcccagc tcagccactg aagaacaggc aaatcaaagc ttccttcaaa    780
taa                                                                 783

<210> SEQ ID NO 17
<211> LENGTH: 783
<212> TYPE: DNA
<213> ORGANISM: Homo sapiens

<400> SEQUENCE: 17
atgtcccatc actgggggta cggcaaacac aacggacctg agcactggca taaggacttc     60
cccattgcca agggagagcg ccagtcccct gttgacatcg acactcatac agccaagtat    120
gacccttccc tgaagcccct gtctgttttcc tatgatcaag caacttccct gaggatcctc    180
aacaatggtc atgctttcaa cgtggagttt gatgactctc aggacaaagc agtgctcaag    240
ggaggacccc tggatggcac ttacagattg attcagttc actttcactg gggttcactt    300
gatggacaag gttcagagca tactgtggat aaaagaaat atgctgcaga acttcacttg    360
gttcactgga acaccaaata tggggatttt gggaaagctg tgcagcaacc tgatggactg    420
gccgttctag gtatttttt gaaggttggc agcgctctac cgggccttca gaaagttgtt    480
gatgtgctgg attccattaa acaaagggc aagagtgctg acttcactaa cttcgatcct    540
cgtggcctcc ttcctgaatc cctggattac tggacctacc caggctcact gaccacccct    600
cctcttctgg aatgtgtgac ctggattgtg ctcaaggaac ccatcagcgt cagcagcgag    660
caggtgttga aattccgtaa acttaacttc aatgggagg gtgaacccga agaactgatg    720
gtggacaact ggcgcccagc tcagccactg aagaacaggc aaatcaaagc ttccttcaaa    780
taa                                                                 783

<210> SEQ ID NO 18
<211> LENGTH: 783
<212> TYPE: DNA
<213> ORGANISM: Homo sapiens

<400> SEQUENCE: 18
atgtcccatc actgggggta cggcaaacac aacggacctg agcactggca taaggacttc     60
cccattgcca agggagagcg ccagtcccct gttgacatcg acactcatac agccaagtat    120
gacccttccc tgaagcccct gtctgttttcc tatgatcaag caacttccct gaggatcctc    180
aacaatggtc atgctttcaa cgtggagttt gatgactctc aggacaaagc agtgctcaag    240
ggaggacccc tggatggcac ttacagattg attcagttc actttcactg gggttcactt    300
gatggacaag gttcagagca tactgtggat aaaagaaat atgctgcaga acttcacttg    360
gttcactgga acaccaaata tggggatttt gggaaagctg tgcagcaacc tgatggactg    420
gccgttctag gtatttttt gaaggttggc agcgctaaac cgggccttca gaaagttgtt    480
gatgcgctgg attccattaa acaaagggc aagagtgctg acttcactaa cttcgatcct    540
cgtggcctcc ttcctgaatc cctggattac tggacctacc caggctcact gaccacccct    600
```

```
cctcttctgg aatgtgtgac ctggattgtg ctcaaggaac ccatcagcgt cagcagcgag      660
caggtgttga aattccgtaa acttaacttc aatggggagg gtgaacccga agaactgatg      720
gtggacaact ggcgcccagc tcagccactg aagaacaggc aaatcaaagc ttccttcaaa      780
taa                                                                    783

<210> SEQ ID NO 19
<211> LENGTH: 783
<212> TYPE: DNA
<213> ORGANISM: Homo sapiens

<400> SEQUENCE: 19
atgtcccatc actgggggta cggcaaacac aacggacctg agcactggca taaggacttc       60
cccattgcca agggagagcg ccagtcccct gttgacatcg acactcatac agccaagtat      120 gaccccttccc tgaagcccct gtctgtttcc tatgatcaag caacttccct gaggatcctc      180
aacaatggtc atgctttcaa cgtggagttt gatgactctc aggacaaagc agtgctcaag      240
ggaggacccc tggatggcac ttacagattg attcagtttc actttcactg gggttcactt      300
gatggacaag gttcagagca tactgtggat aaaaagaaat atgctgcaga acttcacttg      360
gttcactgga acaccaaata tggggatttt gggaaagctg tgcagcaacc tgatggactg      420
gccgttctag gtattttttt gaaggttggc agcgctaaac cgggccttca gaaagttgtt      480
gatgtgctgg attccattaa acaaagggc aagagtgctg acttcactaa cttcgatcct      540
cgtggcctcc ttcctgaatc cctggattac tggacctacc aggctcact gaccacccct      600 cctcttctgg aatgtgtgac ctggattgtg ctcaaggaac ccatcagcgt cagcagcgag      660
caggtgtcga aattccgtaa acttaacttc aatggggagg gtgaacccga agaactgatg      720
gtggacaact ggcgcccagc tcagccactg aagaacaggc aaatcaaagc ttccttcaaa      780
taa                                                                    783

<210> SEQ ID NO 20
<211> LENGTH: 783
<212> TYPE: DNA
<213> ORGANISM: Homo sapiens

<400> SEQUENCE: 20
atgtcccatc actgggggta cggcaaacac aacggacctg agcactggca taaggacttc       60
cccattgcca agggagagcg ccagtcccct gttgacatcg acactcatac agccaagtat      120 gaccccttccc tgaagcccct gtctgtttcc tatgatcaag caacttccct gaggatcctc      180
aacaatggtc atgctttcaa cgtggagttt gatgactctc aggacaaagc agtgctcaag      240
ggaggacccc tggatggcac ttacagattg attcagtttc actttcactg gggttcactt      300
gatggacaag gttcagagca tactgtggat aaaaagaaat atgctgcaga acttcacttg      360
gttcactgga acaccaaata tggggatttt gggaaagctg tgcagcaacc tgatggactg      420
gccgttctag gtattttttt gaaggttggc agcgctaaac cgggccttca gaaagttgtt      480
gatgtgctgg attccattaa acaaagggc aagagtgctg acttcactaa cttcgatcct      540
cgtggcctcc ttcctgaatc cctggattac tggacctacc aggctcact gaccacccct      600 cctcttctgg aatgtgtgac ctggattgtg ctcaaggaac ccatcagcgt cagcagcgag      660
caggtgttga aattccgtaa acttaacttc aatggggagg gtgaacccga agaaccgatg      720
gtggacaact ggcgcccagc tcagccactg aagaacaggc aaatcaaagc ttccttcaaa      780
taa                                                                    783
```

<210> SEQ ID NO 21
<211> LENGTH: 783
<212> TYPE: DNA
<213> ORGANISM: Homo sapiens

<400> SEQUENCE: 21

```
atgtcccatc actgggggta cggcaaacac aacggacctg agcactggca taaggacttc      60
cccattgcca agggagagcg ccagtcccct gttgacatcg acactcatac agccaagtat     120
gacccttccc tgaagcccct gtctgtttcc tatgatcaag caacttccct gaggatcctc     180
aacaatggtc atgctttcaa cgtggagttt gatgactctc aggacaaagc agtgctcaag     240
ggaggacccc tggatggcac ttacagattg attcagtttc actttcactg gggttcactt     300
gatggacaag gttcagagca tactgtggat aaaaagaaat atgctgcaga acttcacttg     360
gttcactgga acaccaaata tggggatttt gggaaagctg tgcagcaacc tgatggactg     420
gccgttctag gtatttttt gaaggttggc agcgctaaac cgggccttca gaaagttgtt     480
gatgtgctgg attccattaa aacaaagggc aagagtgctg acttcactaa cttcgatcct     540
cgtggcctcc ttcctgaatc cctggattac tggacctacc caggctcact gaccacccct     600
cctcttctgg aatgtgtgac ctggattgtg ctcaaggaac ccatcagcgt cagcagcgag     660
caggtgttga aattccgtaa acttaacttc aatggggagg gtgaacccga agaactgatg     720
gtggacaact ggcgcccaac tcagccactg aagaacaggc aaatcaaagc ttccttcaaa     780
taa                                                                  783
```